(12) United States Patent
Liu et al.

(10) Patent No.: US 11,717,501 B2
(45) Date of Patent: Aug. 8, 2023

(54) MAGNESIUM THREONATE COMPOSITIONS AND USES THEREOF

(71) Applicant: Neurocentria, Inc., Walnut Creek, CA (US)

(72) Inventors: Guosong Liu, Oakland, CA (US); Fei Mao, Fremont, CA (US); Jason Gregory Weinger, Concord, CA (US)

(73) Assignee: Neurocentria, Inc., Walnut Creek, CA (US)

( * ) Notice: Subject to any disclaimer, the term of this patent is extended or adjusted under 35 U.S.C. 154(b) by 0 days.

(21) Appl. No.: 16/393,298

(22) Filed: Apr. 24, 2019

(65) Prior Publication Data

US 2019/0328689 A1     Oct. 31, 2019

Related U.S. Application Data

(60) Provisional application No. 62/662,756, filed on Apr. 25, 2018.

(51) Int. Cl.

| | | |
|---|---|---|
| *A01N 43/40* | (2006.01) | |
| *A61K 31/44* | (2006.01) | |
| *C07D 413/04* | (2006.01) | |
| *C07D 413/14* | (2006.01) | |
| *A61K 31/191* | (2006.01) | |
| *A61K 9/00* | (2006.01) | |
| *A61P 25/28* | (2006.01) | |
| *A61K 31/20* | (2006.01) | |
| *A61K 33/06* | (2006.01) | |
| *A61K 47/44* | (2017.01) | |

(52) U.S. Cl.
CPC .......... *A61K 31/191* (2013.01); *A61K 9/0053* (2013.01); *A61K 31/20* (2013.01); *A61K 33/06* (2013.01); *A61K 47/44* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 8,178,118 | B2 | 5/2012 | Liu |
| 8,377,473 | B2 | 2/2013 | Liu |
| 2008/0248137 | A1 | 10/2008 | Liu et al. |
| 2017/0128397 | A1 | 5/2017 | Liu et al. |
| 2017/0258828 | A1 | 9/2017 | Liu et al. |

FOREIGN PATENT DOCUMENTS

| | | |
|---|---|---|
| CN | 102573496 | 7/2012 |
| CN | 105326855 | 2/2016 |
| CN | 106360734 | 2/2017 |
| CN | 107625776 | 1/2018 |
| WO | 2018200885 | 11/2018 |
| WO | 2019209943 | 10/2019 |

OTHER PUBLICATIONS

International Application No. PCT/US2019/028903; International Search Report and Written Opinion of the International Searching Authority, dated Aug. 30, 2019; 10 pages.
Regazzi, M. et al., "Pharmacokinetic Variability and Strategy for Therapeutic Drug Monitoring of Saquinavir (SQV) in HIV-1 Infected Individuals", Br J Clin Pharmacol., 47(4):379-82, (1999).
Sarwar, S. et al., "Development and Evaluation of Sustained Release Losartan Potassium Matrix Tablet Using Kollidon SR as Release Retardant", Braz J Pharm Sci., 48(4):621-8, (2012).
Vacondio, F. et al., "Amino Acid Derivatives as Palmitoylethanolamide Prodrugs: Synthesis, In Vitro Metabolism and In Vivo Plasma Profile in Rats", PLoS One, 10(6):e0128699, (2015).
Zile, M. et al., "Plasma Biomarkers That Reflect Determinants of Matrix Composition Identify the Presence of Left Ventricular Hypertrophy and Diastolic Heart Failure", Circ Heart Fail., 4(3):246-56, (2011).
International Application No. PCT/US2019/028903; International Preliminary Report on Patentability, date of issuance Nov. 5, 2020; 7 pages.

*Primary Examiner* — Layla Soroush
(74) *Attorney, Agent, or Firm* — Rudy J. Ng; Khin K. Chin; Bozicevic, Field & Francis LLP

(57) ABSTRACT

Provided is a dosage form comprising magnesium threonate having enhanced efficacy. Also provided is a pharmacokinetic profile of magnesium threonate having enhanced efficacy. The dosage forms and pharmacokinetic profile of magnesium threonate are used to treat a variety of diseases, disorders, syndromes and/or conditions.

19 Claims, 12 Drawing Sheets

MAGNESIUM THREONATE COMPOSITIONS AND USES THEREOF

Magnesium is the one of the most abundant minerals in the human body and plays multiple roles in maintaining good health. Examples of the roles of magnesium in living cells include homeostasis of other minerals, such as sodium, potassium and calcium, as well as the formation, transfer, storage and utilization of adenosine triphosphate (ATP), a principal source of energy in living cells. Other functions of magnesium in the human body include the maintenance of normal muscle and nerve activity, heart rhythm, bone strength, and immune system health.

It has been estimated that a majority of the people in the U.S. may not be taking sufficient magnesium and hence may be magnesium deficient. Magnesium deficiency including hypomagnesia refers to inadequate intake of dietary magnesium or impaired absorption of magnesium. Magnesium deficiency is also associated with numerous symptoms and diseases, including hypertension, atherosclerosis, arrhythmia, diabetes, and metabolic syndromes. Magnesium deficiency may also be correlated with neurological disorders, including dementia, Alzheimer's disease, and depression.

Typically, magnesium compounds have low bioavailability and are inefficient at increasing magnesium concentrations in the central nervous system (CNS). However, magnesium threonate has high bioavailability relative to other magnesium compounds and is uniquely able to significantly elevate CNS magnesium concentrations. Specifically, magnesium threonate can increase magnesium concentration at neuronal synapses, important for proper synaptic and neurological function. Studies have shown magnesium threonate can alleviate a number of diseases, disorders, syndromes, and conditions. For example, it can improve learning and memory, reduce neuropsychiatric symptoms, reduce neuropathic pain, and prevent cancer cell growth and migration.

SUMMARY

Provided is a dosage form comprising magnesium threonate for the treatment of a disease, disorder, syndrome, or condition in a patient in need thereof, wherein:
(a) at least a portion of magnesium (Mg) and threonate (T) of the magnesium threonate is present in a salt form of $MgT_2$;
(b) the magnesium threonate is present in an amount between about 200 to 6000 mg;
(c) when administered to the patient in need thereof, the dosage form is sufficient to provide an in vivo plasma profile of threonic acid comprising a mean $C_{avg}$ between about 5 µg/mL to about 20 µg/mL.

Also provided is a dosage form comprising magnesium threonate, wherein:
(a) at least a portion of magnesium (Mg) and threonate (T) of the magnesium threonate is present in a salt form of $MgT_2$;
(b) the magnesium threonate is present in an amount between about 200 to 6000 mg; and
(c) the in vivo plasma profile from said dosage form exhibits a fluctuation index that is less than about 170%.

Also provided is a dosage form comprising magnesium threonate, wherein:
(a) at least a portion of magnesium (Mg) and threonate (T) of the magnesium threonate is present in a salt form of $MgT_2$;
(b) the magnesium threonate is present in an amount between about 200 to 6000 mg; and
(c) the release of the magnesium threonate from the dosage form exhibits a first order release constant between about $0.2\ h^{-1}$ and $0.6\ h^{-1}$ calculated from measurements obtained using a USP type II (paddle) dissolution system at 75 rpm, at a temperature of about 37° C.

Also provided is a dosage form comprising magnesium threonate, wherein:
(a) at least a portion of magnesium (Mg) and threonate (T) of the magnesium threonate is present in a salt form of $MgT_2$;
(b) the magnesium threonate is present in an amount at about 17.5 mg/kg LBM/dose; and
(c) when administered to a patient in a fed state, the dosage form is sufficient to provide an in vivo plasma profile of threonic acid comprising:
(i) a mean AUC over 24 hours ($AUC_{0-24}$) of at least about 70 µg·h/mL;
(ii) a mean $C_{max}$ of less than about 13 µg/mL.

Also provided are methods for using the dosage forms described herein for the treatment of a disease, disorder, syndrome, or condition.

Also provided are methods for preparing the dosage forms described herein.

These and other aspects of the invention will be apparent upon reference to the following detailed description. To this end, all publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figure 1A:
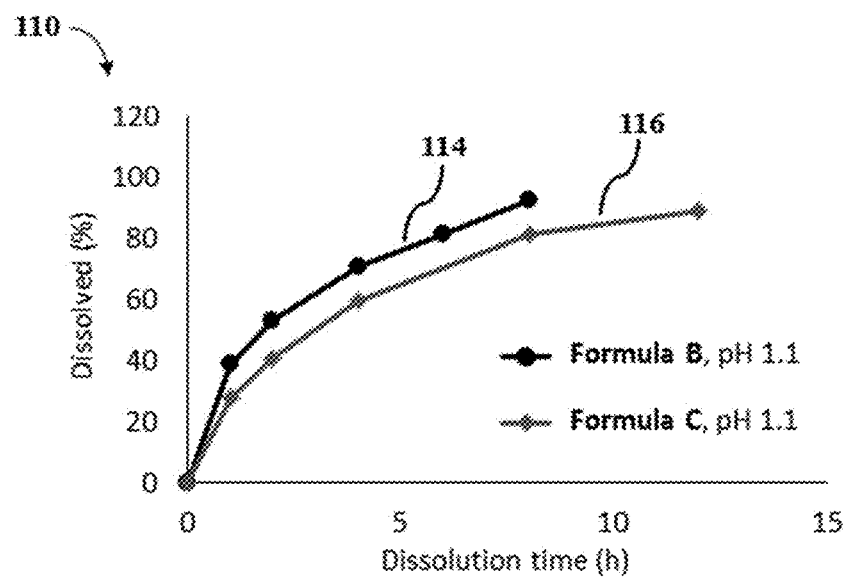
FIG. 1A-1D show threonic acid dissolution profiles of dosage forms comprising magnesium threonate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

Generally, the term "magnesium threonate" refers to in a salt form of $MgT_2$, as illustrated in the formula provided below:

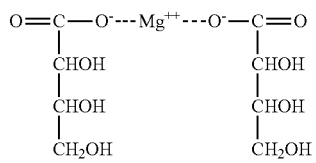

Magnesium threonate also may be referred to as magnesium L-threonate, magnesium (2R,3S)-2,3,4-trihydroxybutanoate, L-Threonic acid Magnesium salt (L-TAMS), MgT, or magtein.

Generally, the term "threonate" means threonate and/or a threonate precursor.

Generally, the term "threonate precursor" means a precursor molecule that can be readily converted to threonate when the composition is dissolved in an aqueous media or ingested as a result of ionization or hydrolysis with or without the aid of an enzyme. The precursor can be a threonic acid, an ester derivative of threonic acid or threonate, or a lactonized threonic acid. Generally, threonate refers to L-threonate. For example, an L-threonate precursor is L-threonic acid, an ester derivative of L-threonic acid or L-threonate, or a lactonized L-threonic acid. In some embodiments, D-threonate or precursors thereof are used.

Generally, the term "elemental magnesium" as used in connection with a magnesium-counter ion compound described herein, refers to a total amount of magnesium that is present as free ion and magnesium that is bound with one or more counter ions. In general, such a term is not used to refer to magnesium that is associated with an agent other than a magnesium-counter ion compound that is a component of a magnesium-counter ion composition (e.g., a pharmaceutical composition, a dietary supplement composition, a foodstuff supplemented with a magnesium-counter ion compound). A small amount of magnesium may be naturally present in or otherwise associated with such an agent. For example, a fruit juice extract or flavoring agent may comprise an amount of magnesium from that naturally present in the fruit from which it was derived.

Generally, the term "bioavailability" refers to the rate and extent to which the active agent, or the active form thereof, is absorbed from a drug product (e.g., an oral dosage form) and becomes available at the site of action. See U.S. Code of Federal Regulations, Title 21, Part 320.1 (2001 ed.). For oral dosage forms, bioavailability generally relates to the processes by which the active ingredient is released from the oral dosage form (e.g., a tablet), converted to the active form (if the active ingredient is not already the active form), and moved to the site of action, e.g., absorbed into the systemic circulation. A change in drug bioavailability attributable to oral dosage forms may be determined by measuring total systemic drug concentrations over time after administration of different oral dosage forms. Drug bioavailability is defined as the area under the curve (AUC). The AUC may be the integrated measure of systemic drug concentrations over time in units of mass-time/volume (e.g., microgram-hour/milliliter, or μg-hour/ml). Alternatively or in addition to, the AUC may be the integrated measure of systemic drug concentrations over a defined, measurable length of time. The AUC over the first 12 or 24 hours following administration of an oral dosage form may be referred to as $AUC_{0-12}$ or $AUC_{0-24}$ respectively.

Generally, the term, $C_{max}$ refers to the peak plasma concentration of a drug.

Generally, the term, $T_{max}$ refers to the time to reach the peak plasma concentration.

Generally, the term $T_{1/2}$ or terminal half-life refers to the time required to divide the plasma concentration of the drug by two after reaching pseudo-equilibrium.

Generally, the term "cognition" refers to a process of obtaining, organizing, understanding, processing, and/or using information or knowledge. Generally, enhancing cognitive function refers to enhancing any aspect of such a process, such as learning, the performance of mental operations, the storage, retrieval, and/or use of information and/or thoughts, memory, and/or preventing a decline of a subject's cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

Generally, a "dissolution profile", i.e., the extent of release of the magnesium and/or threonic acid over a desired time, can be conveniently determined for a given time by measuring the release under controlled conditions, e.g., using a USP dissolution apparatus. Preferred release profiles are those which slow the rate of uptake of the threonic acid and/or magnesium into the blood stream while providing therapeutically effective levels of threonate and/or magnesium. According to standardized dissolution testing guidelines for extended release profiles, dissolution of the active ingredient is measured at given intervals over a period of time. A minimum of three time points is recommended and generally cover early, middle and late stages of the dissolution profile. The last measurement should be no earlier than the time point where at least 80 percent (%) of the active ingredient is dissolved (Guidance for Industry, "Extended Release Oral Dosage Forms: Development, Evaluation, and Application of In Vitro/In Vivo Correlations", Food and Drug Administration, CDER, September 1997, Page 17). Adequate sampling is important: for example, at 1, 2 and 4 hours and every two hours thereafter until 80% of the active ingredient is released (Guidance for Industry, SUPAC-MR: Modified Release Solid Oral Dosage Forms," Food and Drug Administration, CDER, September 1997, Page 6). The preferred dissolution apparatus is USP apparatus I (basket) or II (paddle), used at recognized rotation speeds, e.g., 100 revolutions per minute (rpm for the basket and 50-75 rpm for the paddle (Guidance for Industry, "Extended Release Oral Dosage Forms: Development, Evaluation, and Application of In Vitro/In Vivo Correlations", Food and Drug Administration, CDER, September 1997, Page 4). Extended release dosage forms permit the release of the active ingredient over an extended period of time. On the other hand, materials which dissolve at least 80% in the first 30 to 60 minutes in solution qualify as immediate release (IR) profiles. ("Dissolution Testing of Immediate Release Solid Oral Dosage Forms", issued August 1997, Section IV-A).

Generally, the term "dose proportional" as used herein refers to the relationship between the dose of an active ingredient and its bioavailability. For example, dose proportionality exists if twice as much of the same composition will deliver twice the active ingredient and provide the same bioavailability as one dose of the dosage form. The dose proportionality applies to a wide range of doses as discussed in detail herein.

Generally, the term "effective amount" in reference to an active agent refers to the amount of the active agent sufficient to elicit a particular biological condition, effect, and/or response. The absolute amount of a particular agent that is effective in this manner may vary depending on various factors, such as the desired biological endpoint, the agent itself, the subject or targeted part thereof, and/or the like, for example. An effective amount of an active agent may be administered in a single dose or in multiple doses. Examples of a biological condition, effect or response that may result from an effective amount of an active agent include a maintaining and/or improving of a subject's performance of a task involving or associated with cognitive function, a maintaining and/or improving of a subject's performance in a test that measures something relating to or associated with cognitive function, a maintaining and/or improving (slowing, for example) of a rate of decline in cognitive function, and/or the like, for example. A component may be described herein as having at least an effective amount, or at least an amount effective, such as that associated with a particular goal or purpose, such as any described herein.

Generally, the term "fasted state" refers to a dietary state of the subject, in which the patient consumes a standard meal and fasts for about 6 hours (h), 7 h, 8 h, 9 h, 10 h, 11 h, 12 h, 6 to 10 h, 8 to 12 h, or 6 to 16 h prior to administration of a dosage form. The patient may fast about an additional 4 hours post-dose.

Generally, the term "fed state" refers to a dietary state of the subject, in which the patient consumes a standard meal, fasts for about 6 h, 7 h, 8 h, 9 h, 10 h, 11 h, 12 h, 6 to 10 h, 8 to 12 h, or 6 to 16 h, and consumes another meal at about 30 minutes prior to administration of a dosage form. The patient may fast about an additional 4 hours post-dose.

Generally, the term "fluctuation value" refers to the difference between the peak plasma concentration of the drug ($C_{max}$) and the minimum plasma concentration ($C_{min}$) that the drug achieves after the drug has been administrated and prior to the administration of a second dose. Not wishing to be bound by theory, a lower fluctuation value may indicate a more steady state bioavailability of the active agent.

Generally, the term "fluctuation index" refers to fluctuation value ($C_{max}$-$C_{min}$) as a percent of $C_{avg}$, i.e., (($C_{max}$-$C_{min}$)/$C_{avg}$)*100% where $C_{avg}$ refers to AUC/time interval.

Generally, the term "modified-release" refers to a mechanism that delivers a drug with a delay after its administration (delayed-release dosage) or for a prolonged period of time (extended-release dosage) or to a specific target in the body (targeted-release dosage). Extended-release includes sustained-release and controlled-release. Sustained-release refers to maintaining drug release over a sustained period of time but not at a constant rate, e.g., first order release. Controlled-release refers to maintaining drug release over a sustained period of time at a nearly constant rate, e.g., zero order release.

Generally, the term "pharmacokinetics" (PK) refers to the study of the fate of pharmaceuticals from the time they are ingested until they are eliminated from the body. The sequence of events for an oral composition may include absorption through the various mucosal surfaces, distribution via the blood stream to various tissues, biotransformation in the liver and other tissues, action at the target site, and elimination of drug or metabolites in urine or bile.

Generally, the term "physiologically acceptable," or "pharmaceutically acceptable," refers to biologically or pharmacologically compatible for in vivo use in animals or humans, e.g., approved by a regulatory agency of the Federal or a state government or listed in the U.S. Pharmacopeia or other generally recognized pharmacopeia for use in animals, and more particularly in humans.

Generally, the term "oral dose" or "oral dosage form" refers to any orally administered composition that contains magnesium (Mg) and threonate (T) as an active agent. In some cases, an oral dosage form includes a single type of oral dosage form (e.g., a tablet, gel, etc.). Each of the single type of oral dosage form may include one or more unit doses or include 1 to 10 unit doses (e.g., 1 to 10 tablets), 1 to 5 unit doses, or 1 to 3 unit doses. The unit doses can take on a format of a tablet, pill, gel, capsule, soft gelatin capsules, or any other formats disclosed herein or known in the art. In some cases, an oral dosage form includes two or more types of oral dosage forms (e.g., a pill and a tablet), or 2 to 5 types of oral dosage forms. Each of the two or more types of oral dosage forms may include one or more unit doses (e.g., a pill and two tablets, two pills and a tablet, two pills and two tablets, etc.).

Generally, the term "systemic drug concentration" refers to a drug concentration in a mammal's bodily fluids, such as blood or plasma, serum, urine, saliva, and/or other easily sampled bodily fluids. The term may also include drug concentrations in tissues bathed by the systemic fluids, including the skin.

Generally, the term "skewness" refers to a characterization of the degree of asymmetry of the plasma concentration profile around the mean plasma concentration value.

Generally, the term "subject" refers to any animal. Examples of such animals include, but are not limited to, cold-blooded animals, warm-blooded animals, mammals, domesticated mammals, primates, humans, and individuals or a patient to whom a composition is to be administered for experimental, diagnostic, nutritional, and/or therapeutic purposes. A subject or patient may be a subject or patient of normal, good, or excellent health, mood, cognitive, and/or nutritional status, or of compromised health, mood, cognitive, and/or nutritional status, including of abnormal, poor, damaged, unhealthy, impaired, diseased, and/or nutritionally deficient status. The subject may be of any age, including advanced age.

As used herein the term "tablet" refers generally to tablets, caplets, capsules, including soft gelatin capsules, and lozenges.

As used herein, the term "treat", in all its verb forms, included to relieve or alleviate at least one symptom of a disorder in a subject, the disorder including, e.g., pain, Alzheimer's disease, vascular dementia, or Parkinson's disease. The term "treat" may mean to relieve or alleviate the intensity and/or duration of a manifestation of a disorder experienced by a patient in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognition. The term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. The dementia is associated with a CNS disorder, including without limitation neurodegenerative diseases such as Alzheimer's disease (AD), Down's Syndrome and cerebrovascular dementia (VaD). The term "treatment" includes the act of "treating" as defined above.

Provided are dosage forms that contain magnesium (Mg) and threonate (T), formulated and/or administered to provide a serum or plasma concentration over a desired time period that is high enough to be physiologically effective but at any given time, not too high such that it triggers adverse events or reduces physiological effects.

Figure 8:
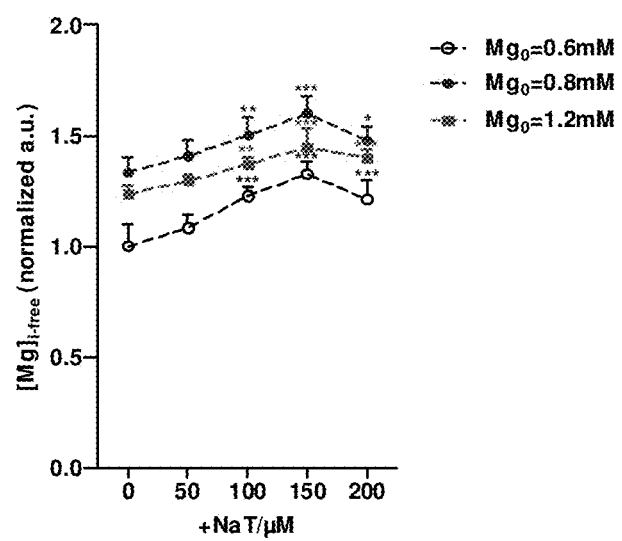
FIG. 8 shows a dose response curve for magnesium threonate.

The dose response curve for magnesium threonate has a bell shape (FIG. 8), such that efficacy is diminished when dosage increases above a certain point. The concentration range for magnesium threonate to achieve a therapeutic response is relatively small. This unique property of magnesium threonate indicates that for a given AUC, efficacy could be affected by the shape of the serum or plasma concentration profile. For a dosage form, sustained release of the magnesium threonate may be used for reducing and delaying the peak plasma level while maintaining physiologically effective blood concentrations. A sustained release formulation has lower fluctuation than both fast release and zero-order controlled release dosage forms (Table 2), resulting in better efficacy (see, e.g., FIG. 5). Furthermore, as a result of the delay in the time to obtain peak serum or plasma level and the extended period of time at the therapeutically effective serum or plasma level, the dosage frequency can be reduced to, for example, once or twice daily dosage, thereby improving subject compliance and adherence. Reducing the concentration fluctuation also reduces the concentration of the active ingredient at its maximum time point and provides a more constant amount of magnesium threonate to the subject being treated over a given period of time.

Provided is a dosage form comprising magnesium threonate for the treatment of a disease, disorder, syndrome, or condition in a patient in need thereof, wherein:
 (a) at least a portion of magnesium (Mg) and threonate (T) of the magnesium threonate is present in a salt form of $MgT_2$;
 (b) the magnesium threonate is present in an amount between about 200 to 6000 mg;
 (c) when administered to the patient in need thereof, the dosage form is sufficient to provide an in vivo plasma profile of threonic acid comprising a mean $C_{avg}$ between about 5 µg/mL to about 20 µg/mL.

Also provided is a dosage form comprising magnesium threonate, wherein:
 (a) at least a portion of magnesium (Mg) and threonate (T) of the magnesium threonate is present in a salt form of $MgT_2$;
 (b) the magnesium threonate is present in an amount between about 200 to 6000 mg; and
 (c) the in vivo plasma profile from said dosage form exhibits a fluctuation index that is less than about 170%.

Also provided is a dosage form comprising magnesium threonate, wherein:
 (a) at least a portion of magnesium (Mg) and threonate (T) of the magnesium threonate is present in a salt form of $MgT_2$;
 (b) the magnesium threonate is present in an amount between about 200 to 6000 mg; and
 (c) the release of the magnesium threonate from the dosage form exhibits a first order release constant between about 0.2 $h^{-1}$ and 0.6 $h^{-1}$ calculated from measurements obtained using a USP type II (paddle) dissolution system at 75 rpm, at a temperature of about 37° C.

Also provided is a dosage form comprising magnesium threonate, wherein:
 (a) at least a portion of magnesium (Mg) and threonate (T) of said magnesium threonate is present in a salt form of $MgT_2$;
 (b) said magnesium threonate is present in an amount between about 200 to 6000 mg; and
 (c) in vivo plasma profile from said dosage form exhibits a skewness that is less than about 0.2.

Also provided is a dosage form comprising magnesium threonate, wherein:
 (a) at least a portion of magnesium (Mg) and threonate (T) of the magnesium threonate is present in a salt form of $MgT_2$;
 (b) the magnesium threonate is present in an amount at about 17.5 mg/kg LBM/dose; and (c) when administered to a patient in a fed state at a therapeutic dosage, the dosage form is sufficient to provide an in vivo plasma profile of threonic acid comprising:
  (i) a mean AUC over 24 hours ($AUC_{0-24}$) of at least about 70 μg·h/mL; and
  (ii) a mean $C_{max}$ of less than about 13 μg/mL.

In some embodiments, the dosage form is formulated for oral administration. In some embodiments, the dosage form is sufficient to provide an in vivo plasma profile of threonic acid comprising a mean $T_{max}$ of at least about 4.5 hours.

In some embodiments, the dosage form is liquid, semi-liquid, semi-solid, or solid. In some embodiments, the dosage form is a gel, pill, tablet, capsule, bead, emulsion, granule, paste, prill, powder, syrup, suspension, slurry, or aerosol.

In some embodiments, the dosage form comprises at least 2 or more unit doses, e.g., two tablets are administered at the same time. When comprising two or more unit doses, each unit dose exhibits substantially the same in vitro dissolution profile in a dissolution medium. Alternatively, when comprising two or more unit dose, each unit dose exhibits different in vitro dissolution profiles in a dissolution medium. In some embodiments, the dosage form includes three identical tablets, and the three identical tablets exhibit substantially the same in vitro dissolution profile in a dissolution medium. In some embodiments, the dosage form includes one tablet and one capsule, and the tablet and the capsule exhibit different in vitro dissolution profiles in a dissolution medium. In some embodiments, the dosage form comprises two or more individual unit doses, wherein each unit dose exhibits substantially the same in vitro dissolution profile in a dissolution medium.

In some embodiments, the release of the magnesium threonate from the dosage form exhibits a first order release constant between about 0.2 $h^{-1}$ and 0.6 $h^{-1}$ calculated from measurements obtained using a USP type II (paddle) dissolution system at 75 rpm, at a temperature of about 37° C. In some embodiments, the first order release constant is between about 0.25 and 0.45 calculated from measurements obtained using a USP type II (paddle) dissolution system at 75 rpm, at a temperature of about 37° C. In some embodiments, the first order release constant is between about 0.3 $h^{-1}$ and 0.4 $h^{-1}$ calculated from measurements obtained using a USP type II (paddle) dissolution system at 75 rpm, at a temperature of about 37° C.

In some embodiments, the in vivo plasma profile from said dosage form exhibits a fluctuation index that is less than about 170%. In some embodiments, the in vivo plasma profile from said dosage form exhibits a fluctuation index that is less than about 165%. In some embodiments, the in vivo plasma profile from said dosage form exhibits a fluctuation index that is less than about 160%. In some embodiments, the in vivo plasma profile from said dosage form exhibits a fluctuation index that is less than about 155%.

In some embodiments, the in vivo plasma profile from said dosage form exhibits a skewness that is less than about 0.2.

In some embodiments, the first order release constant is between about 0.25 $h^{-1}$ and 0.45 $h^{-1}$ calculated from measurements obtained using a USP type II (paddle) dissolution system at 75 rpm, at a temperature of about 37° C. and the in vivo plasma profile from said dosage form exhibits a fluctuation index that is less than about 170%. In some embodiments, the first order release constant is between about 0.3 $h^{-1}$ and 0.4 $h^{-1}$ calculated from measurements obtained using a USP type II (paddle) dissolution system at 75 rpm, at a temperature of about 37° C. and the in vivo plasma profile from said dosage form exhibits a fluctuation index that is less than about 170%.

In some embodiments, when administered to a patient in a fed state, the dosage form is sufficient to provide an in vivo plasma profile of threonic acid comprising a mean fluctuation value of less than about 14 μg/mL. In some embodiments, the dosage form provides a mean fluctuation value ($C_{max}-C_{min}$) of less than about 14 μg/mL, 13 μg/mL, 12 μg/mL, 11 μg/mL, 10 μg/mL, 9 μg/mL, 8 μg/mL, 7 μg/mL, 6 μg/mL, 5 μg/mL, or lower. In some embodiments, fluctuation value ($C_{max}-C_{min}$) is from about 14 μg/mL to about 5 μg/mL, from about 12 μg/mL to about 8 μg/mL, from about 11 μg/mL to about 9 μg/mL, from about 11 μg/mL to about 10 μg/mL. In some embodiments, the dosage form provides an in vivo plasma profile of threonic acid comprising the mean fluctuation value of less than about 10 μg/mL per gram of administered magnesium threonate. In some embodiments, when administered to a patient in a fed state, the dosage form is sufficient to provide an in vivo plasma profile of threonic acid comprising the mean fluctuation value of less than about 10 μg/mL per gram of administered magnesium threonate.

Figure 3:
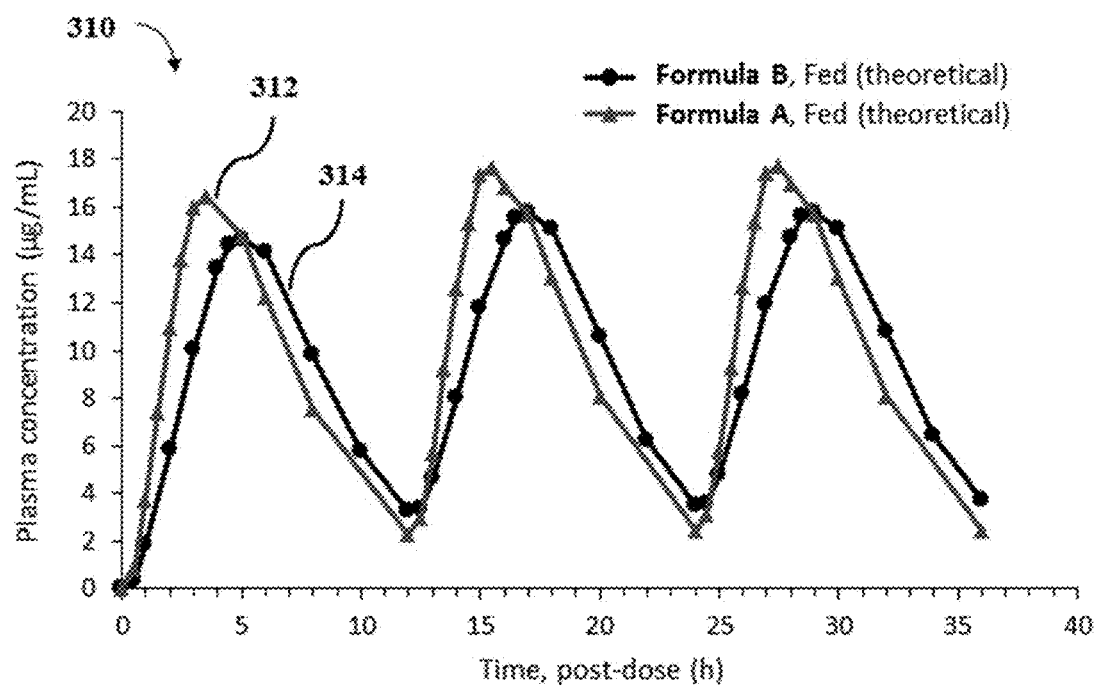
FIG. 3 shows model plasma concentration profiles from theoretical repeated dosing of dosage forms comprising magnesium threonate.

A model graph indicates that a theoretical administration of Formula B at every 12 hours may yield a lower fluctuation value (10.9) than that of Formula A (14.2) (FIG. 3).

In some embodiments, the in vitro dissolution profile of the dosage form in the dissolution medium ranges between about 10 to 50% in about 1 hour. In some embodiments, the in vitro dissolution profile of the dosage form in the dissolution medium ranges between about 10 to 60% in about 2 hours. In some embodiments, the in vitro dissolution profile of the dosage form in the dissolution medium ranges between about 20 to 80% in about 4 hours. In some embodiments, the in vitro dissolution profile of the dosage form in the dissolution medium ranges between about 50 to 90% in about 6 hours. In some embodiments, the in vitro dissolution profile of the dosage form in the dissolution medium ranges between (i) about 10 to 50% in about 1 hour, (ii) about 10 to 60% in about 2 hours, (iii) about 20 to 80% in about 4 hours, (iv) about 50 to 90% in about 6 hours, and (v) greater or equal to about 80% in about 8 hours as measured using a USP type II (paddle) dissolution system at 75 rpm, at a temperature of about 37° C.

In some embodiments, when administered to the patient in need thereof, the dosage form is sufficient to provide an in vivo plasma profile of threonic acid comprising a mean $C_{avg}$ of between about 5 μg/mL to about 20 μg/mL. In some embodiments, when administered to the patient in need thereof, the dosage form is sufficient to provide an in vivo plasma profile of threonic acid comprising a mean $C_{avg}$ of between about 5 μg/mL to about 15 μg/mL.

In some embodiments, the dosage form provides an in vivo plasma profile of threonic acid comprising the mean $AUC_{0-24}$ is at least about 55 μg·h/mL based on a dosage of 17.5 mg/kg LBM/dose. In some embodiments, when administered to a patient in a fed state, the dosage form is sufficient to provide an in vivo plasma profile of threonic acid comprising the mean $AUC_{0-24}$ of at least about 55 μg·h/mL based on a dosage of 17.5 mg/kg LBM/dose. In some embodiments, the dosage form is formulated such that when administered in vivo, it provides an in vivo plasma profile of threonic acid comprising a mean AUC over 24 hours ($AUC_{0-24}$) of at least about 50 μg·h/mL, 80 μg·h/mL, 90 μg·h/mL, 100 μg·h/mL, 110 μg·h/mL, 120 μg·h/mL, 130 μg·h/mL, 140 μg·h/mL, 150 μg·h/mL, 160 μg·h/mL, 170 μg·h/mL, 180 μg·h/mL, 190 μg·h/mL, 200 μg·h/mL, 300

μg·h/mL, 400 μg·h/mL, 500 μg·h/mL or more. In some embodiments, $AUC_{0-24}$ is from about 100 μg·h/mL to about 500 μg·h/mL, about 100 μg·h/mL to about 200 μg·h/mL, or about 103 μg·h/mL to about 120 μg·h/mL. In some embodiments, the percentage fluctuation between $AUC_{0-24}$ measured under fed condition to fasted condition (($AUC_{0-24}$ fed−$AUC_{0-24}$ fasted)/$AUC_{0-24}$ fasted) is at least greater than 50%, 100%, 150% or more. In some embodiments, the absolute fluctuation between $AUC_{0-24}$ measured under fed condition to fasted condition is at least about 20 μg·h/mL, 25 μg·h/mL, 30 μg·h/mL, 35 μg·h/mL, or more.

In some embodiments, the dosage form provides an in vivo plasma profile of threonic acid comprising a mean $C_{max}$ of less than about 13 μg/mL based on a dosage of 17.5 mg/kg LBM/dose. In some embodiments, when administered to a patient in a fed state, the dosage form is sufficient to provide an in vivo plasma profile of threonic acid comprising a mean $C_{max}$ of less than about 13 μg/mL based on a dosage of 17.5 mg/kg LBM/dose.

In some embodiments, the dosage form provides an in vivo plasma profile of threonic acid comprising a mean $C_{max}$ of less than about 12 μg/mL, 11 μg/mL, 10 μg/mL, 9 μg/mL, 8 μg/mL, 7 μg/mL, 6 μg/mL, or 5 μg/mL. In some embodiments, the dosage form provides an in vivo plasma profile of threonic acid comprising a mean $C_{max}$ from about 17 μg/mL to about 10 μg/mL, from about 17 μg/mL to about 15 μg/mL, from about 16 μg/mL to about 10 μg/mL, from about 16 μg/mL to about 12 μg/mL.

In some embodiments, the dosage form provides an in vivo plasma profile of threonic acid comprising a mean $T_{max}$ of at least about 4.5 hours (h), 5 h, 5.5 h, 6 h, 6.5 h, 7 h, 7.5 h, 8 h, 8.5 h, 9 h, 9.5 h, 10 h or greater.

In some embodiments, the dosage form is sufficient to provide at least about 15 to 30 mg/kg of lean body mass/dose of magnesium threonate (30-60 mg/kg LBM/day), given every 12 hours in a patient in need of treatment of a disease, disorder, syndrome, or condition. In some embodiments, the dosage form is sufficient to provide at least about 15 mg/kg of lean body mass/dose of magnesium threonate, given every 12 hours in a patient in need of treatment of a disease, disorder, syndrome, or condition. In some embodiments, the dosage form is sufficient to provide at least about 15 mg/kg of lean body mass/dose of magnesium threonate, given every 24 hours in a patient in need of treatment of a disease, disorder, syndrome, or condition. In some embodiments, the dosage form is sufficient to provide at about 10 to 30 mg/kg of lean body mass/dose of magnesium threonate, given every 24 hours in a patient in need of treatment of a disease disorder, syndrome and/or condition. In some embodiments, the dosage form is sufficient to provide at least about 30 mg/kg of lean body mass/day of magnesium threonate. In some embodiments, the dosage form is sufficient to provide about 20 to 60 mg/kg of lean body mass/day of magnesium threonate.

In some embodiments, the dosage form is sufficient to provide magnesium threonate in an amount of about 35 mg/kg LBM/day to about 50 mg/kg LBM/day. In some embodiments, the dosage form is sufficient to provide magnesium threonate in an amount of at least about 35 mg/kg LBM/day. In some embodiments, the dosage form is sufficient to provide magnesium threonate in an amount of at most about 50 mg/kg LBM/day. In some embodiments, the dosage form is sufficient to provide magnesium threonate in an amount of about 35 mg/kg LBM/day to about 36 mg/kg LBM/day, about 35 mg/kg LBM/day to about 37 mg/kg LBM/day, about 35 mg/kg LBM/day to about 38 mg/kg LBM/day, about 35 mg/kg LBM/day to about 39 mg/kg LBM/day, about 35 mg/kg LBM/day to about 40 mg/kg LBM/day, about 35 mg/kg LBM/day to about 42 mg/kg LBM/day, about 35 mg/kg LBM/day to about 44 mg/kg LBM/day, about 35 mg/kg LBM/day to about 46 mg/kg LBM/day, about 35 mg/kg LBM/day to about 48 mg/kg LBM/day, about 35 mg/kg LBM/day to about 50 mg/kg LBM/day, about 36 mg/kg LBM/day to about 37 mg/kg LBM/day, about 36 mg/kg LBM/day to about 38 mg/kg LBM/day, about 36 mg/kg LBM/day to about 39 mg/kg LBM/day, about 36 mg/kg LBM/day to about 40 mg/kg LBM/day, about 36 mg/kg LBM/day to about 42 mg/kg LBM/day, about 36 mg/kg LBM/day to about 44 mg/kg LBM/day, about 36 mg/kg LBM/day to about 46 mg/kg LBM/day, about 36 mg/kg LBM/day to about 48 mg/kg LBM/day, about 36 mg/kg LBM/day to about 50 mg/kg LBM/day, about 37 mg/kg LBM/day to about 38 mg/kg LBM/day, about 37 mg/kg LBM/day to about 39 mg/kg LBM/day, about 37 mg/kg LBM/day to about 40 mg/kg LBM/day, about 37 mg/kg LBM/day to about 42 mg/kg LBM/day, about 37 mg/kg LBM/day to about 44 mg/kg LBM/day, about 37 mg/kg LBM/day to about 46 mg/kg LBM/day, about 37 mg/kg LBM/day to about 48 mg/kg LBM/day, about 37 mg/kg LBM/day to about 50 mg/kg LBM/day, about 38 mg/kg LBM/day to about 39 mg/kg LBM/day, about 38 mg/kg LBM/day to about 40 mg/kg LBM/day, about 38 mg/kg LBM/day to about 42 mg/kg LBM/day, about 38 mg/kg LBM/day to about 44 mg/kg LBM/day, about 38 mg/kg LBM/day to about 46 mg/kg LBM/day, about 38 mg/kg LBM/day to about 48 mg/kg LBM/day, about 38 mg/kg LBM/day to about 50 mg/kg LBM/day, about 39 mg/kg LBM/day to about 40 mg/kg LBM/day, about 39 mg/kg LBM/day to about 42 mg/kg LBM/day, about 39 mg/kg LBM/day to about 44 mg/kg LBM/day, about 39 mg/kg LBM/day to about 46 mg/kg LBM/day, about 39 mg/kg LBM/day to about 48 mg/kg LBM/day, about 39 mg/kg LBM/day to about 50 mg/kg LBM/day, about 40 mg/kg LBM/day to about 42 mg/kg LBM/day, about 40 mg/kg LBM/day to about 44 mg/kg LBM/day, about 40 mg/kg LBM/day to about 46 mg/kg LBM/day, about 40 mg/kg LBM/day to about 48 mg/kg LBM/day, about 40 mg/kg LBM/day to about 50 mg/kg LBM/day, about 42 mg/kg LBM/day to about 44 mg/kg LBM/day, about 42 mg/kg LBM/day to about 46 mg/kg LBM/day, about 42 mg/kg LBM/day to about 48 mg/kg LBM/day, about 42 mg/kg LBM/day to about 50 mg/kg LBM/day, about 44 mg/kg LBM/day to about 46 mg/kg LBM/day, about 44 mg/kg LBM/day to about 48 mg/kg LBM/day, about 44 mg/kg LBM/day to about 50 mg/kg LBM/day, about 46 mg/kg LBM/day to about 48 mg/kg LBM/day, about 46 mg/kg LBM/day to about 50 mg/kg LBM/day, or about 48 mg/kg LBM/day to about 50 mg/kg LBM/day. In some embodiments, the dosage form is sufficient to provide magnesium threonate in an amount of about 35 mg/kg LBM/day, about 36 mg/kg LBM/day, about 37 mg/kg LBM/day, about 38 mg/kg LBM/day, about 39 mg/kg LBM/day, about 40 mg/kg LBM/day, about 42 mg/kg LBM/day, about 44 mg/kg LBM/day, about 46 mg/kg LBM/day, about 48 mg/kg LBM/day, or about 50 mg/kg LBM/day.

In some embodiments, the dosage form is sufficient to provide magnesium threonate in an amount of at least about 24 mg/kg TBW/day, 25 mg/kg TBW/day, 26 mg/kg TBW/day, 27 mg/kg TBW/day, 28 mg/kg TBW/day, 29 mg/kg TBW/day, 30 mg/kg TBW/day, 31 mg/kg TBW/day, 32 mg/kg TBW/day, 33 mg/kg TBW/day, 34 mg/kg TBW/day, 35 mg/kg TBW/day or more. In some embodiments, the dosage form is sufficient to provide magnesium threonate in an amount of at most about 35 mg/kg TBW/day, 34 mg/kg TBW/day, 33 mg/kg TBW/day, 32 mg/kg TBW/day, 21 mg/kg TBW/day, 30 mg/kg TBW/day, 29 mg/kg TBW/day, 28 mg/kg TBW/day, 27 mg/kg TBW/day, 26 mg/kg TBW/day, 25 mg/kg TBW/day, 24 mg/kg TBW/day or less.

In some embodiments, the $MgT_2$ is present in an amount equal to at least about 20 milligram (mg) of magnesium (Mg) by weight. In some embodiments, the magnesium (Mg) is present in an amount greater than about 1%, 2%, 3%, 4%, 5%, 6%, 7%, 8%, 9%, 10%, 11%, 12%, 13%, 14%, 15% or more by weight. In some embodiments, the magnesium (Mg) is present in an amount greater than about 1%, 5%, or greater than about 7% by weight. In some embodiments, the average tablet size for round tablets is about 10 mg to 150 mg elemental Mg and for capsule-shaped tablets about 20 mg to 200 mg elemental Mg.

In some embodiments, the molar ratio between the threonate (T) and the magnesium (Mg) is greater than or equal to about 0.1 to 2.

In some embodiments, the dosage form comprises magnesium threonate in an amount of at least about 200 mg. In some embodiments, the dosage form comprises magnesium threonate in an amount of at most about 6,000 mg. In some embodiments, the dosage form comprises magnesium threonate in an amount of about 200 mg to about 6,000 mg. In some embodiments, the magnesium threonate is present in an amount between about 200 to 4000 mg. In some embodiments, the dosage form comprises magnesium threonate in an amount of about 200 mg to about 300 mg, about 200 mg to about 400 mg, about 200 mg to about 500 mg, about 200 mg to about 1,000 mg, about 200 mg to about 1,500 mg, about 200 mg to about 2,000 mg, about 200 mg to about 2,500 mg, about 200 mg to about 3,000 mg, about 200 mg to about 4,000 mg, about 200 mg to about 5,000 mg, about 200 mg to about 6,000 mg, about 300 mg to about 400 mg, about 300 mg to about 500 mg, about 300 mg to about 1,000 mg, about 300 mg to about 1,500 mg, about 300 mg to about 2,000 mg, about 300 mg to about 2,500 mg, about 300 mg to about 3,000 mg, about 300 mg to about 4,000 mg, about 300 mg to about 5,000 mg, about 300 mg to about 6,000 mg, about 400 mg to about 500 mg, about 400 mg to about 1,000 mg, about 400 mg to about 1,500 mg, about 400 mg to about 2,000 mg, about 400 mg to about 2,500 mg, about 400 mg to about 3,000 mg, about 400 mg to about 4,000 mg, about 400 mg to about 5,000 mg, about 400 mg to about 6,000 mg, about 500 mg to about 1,000 mg, about 500 mg to about 1,500 mg, about 500 mg to about 2,000 mg, about 500 mg to about 2,500 mg, about 500 mg to about 3,000 mg, about 500 mg to about 4,000 mg, about 500 mg to about 5,000 mg, about 500 mg to about 6,000 mg, about 1,000 mg to about 1,500 mg, about 1,000 mg to about 2,000 mg, about 1,000 mg to about 2,500 mg, about 1,000 mg to about 3,000 mg, about 1,000 mg to about 4,000 mg, about 1,000 mg to about 5,000 mg, about 1,000 mg to about 6,000 mg, about 1,500 mg to about 2,000 mg, about 1,500 mg to about 2,500 mg, about 1,500 mg to about 3,000 mg, about 1,500 mg to about 4,000 mg, about 1,500 mg to about 5,000 mg, about 1,500 mg to about 6,000 mg, about 2,000 mg to about 2,500 mg, about 2,000 mg to about 3,000 mg, about 2,000 mg to about 4,000 mg, about 2,000 mg to about 5,000 mg, about 2,000 mg to about 6,000 mg, about 2,500 mg to about 3,000 mg, about 2,500 mg to about 4,000 mg, about 2,500 mg to about 5,000 mg, about 2,500 mg to about 6,000 mg, about 3,000 mg to about 4,000 mg, about 3,000 mg to about 5,000 mg, about 3,000 mg to about 6,000 mg, about 4,000 mg to about 5,000 mg, about 4,000 mg to about 6,000 mg, or about 5,000 mg to about 6,000 mg. In some embodiments, the dosage form comprises magnesium threonate in an amount of about 200 mg, about 300 mg, about 400 mg, about 500 mg, about 1,000 mg, about 1,500 mg, about 2,000 mg, about 2,500 mg, about 3,000 mg, about 4,000 mg, about 5,000 mg, or about 6,000 mg.

In some embodiments, the magnesium threonate is present in an amount of less than about 77.5% by weight in the dosage form. In some embodiments, the magnesium threonate is present in an amount of less than about 77% by weight. In some embodiments, the magnesium threonate is present in an amount of between about 40 and about 77% wt/wt. In some embodiments, the magnesium threonate is present in an amount of between about 45 and about 70% wt/wt. In some embodiments, the magnesium threonate is present in an amount of about 70%. In some embodiments, the magnesium threonate is present in an amount of about 53%.

In some embodiments, the dosage form further comprises carnauba wax as a binder. In some embodiments, the carnauba wax is present in an amount of between about 10 and about 30% wt/wt. In some embodiments, the carnauba wax is present in an amount of about 28% wt/wt. In some embodiments, the carnauba wax is present in an amount of about 10% wt/wt.

In some embodiments, the dosage form further comprises a lubricant. The lubricant comprises, for example, calcium stearate or magnesium stearate. In some embodiments, the dosage form further comprises magnesium stearate as a lubricant. In some embodiments, the magnesium stearate is present in an amount of between about 1 and about 3% wt/wt. In some embodiments, the magnesium stearate is present in an amount of between about 1 and about 2% wt/wt. In some embodiments, the magnesium stearate is present in an amount of about 1.4% wt/wt. In some embodiments, the magnesium stearate is present in an amount of about 2% wt/wt.

In some embodiments, the dosage form further comprises carnauba wax and magnesium stearate. In some embodiments, a weight ratio of the carnauba wax to the magnesium stearate is greater than about 12. In some embodiments, a weight ratio of the carnauba wax to the magnesium stearate is at least about 13. The weight ratio of the carnauba wax to the magnesium stearate is at least about 13, 13.5, 14, 14.5, 15, 16, 17, 18, 19, 20, 30, 40, 50 or more. In some embodiments, a weight ratio of the carnauba wax to the magnesium stearate is about 20. In some embodiments, the carnauba wax and the magnesium stearate, in combination, are present in an amount of at least about 22.5% by weight in the dosage form.

In some embodiments, a weight ratio of the carnauba wax to the magnesium stearate is less than about 8. In some embodiments, a weight ratio of the carnauba wax to the magnesium stearate is between about 4 and 8. In some embodiments, a weight ratio of the carnauba wax to the magnesium stearate is between about 4 and 6. In some embodiments, a weight ratio of the carnauba wax to the magnesium stearate is about 5.

In some embodiments, the magnesium threonate is present in an amount of less than about 77% by weight, and a combination of the carnauba wax and the magnesium stearate is present in an amount of at least about 23% by weight. In some embodiments, the magnesium threonate is present in an amount of about 77%, 76%, 75%, 74%, 73%, 72%, 71%, 70%, 60%, 50%, 40% 30%, 20%, 10% or less by weight. Alternatively or in addition to, the combination of the carnauba wax and the magnesium stearate is present in an amount of at least 23%, 24%, 25%, 26%, 27%, 28%, 29%, 30%, 40%, 50%, 60%, 70%, 90%, 90% or more by weight.

In some embodiments, the magnesium threonate is present in an amount of less than about 77% by weight, and a combination of the carnauba wax and the magnesium stearate is present in an amount of less than about 15% by weight. In some embodiments, the magnesium threonate is present in an amount of less than about 60% by weight, and a combination of the carnauba wax and the magnesium stearate is present in an amount of less than about 15% by weight. In some embodiments, the magnesium threonate is present in an amount of between about 40% and 60% by weight, and a combination of the carnauba wax and the magnesium stearate is present in an amount of between about 10% and 15% by weight. In some embodiments, the magnesium threonate is present in an amount of between about 50% and 55% by weight, and a combination of the carnauba wax and the magnesium stearate is present in an amount of between about 10% and 15% by weight. In some embodiments, the magnesium threonate is present in an amount of about 53% by weight, and a combination of the carnauba wax and the magnesium stearate is present in an amount of between about 12% by weight.

In some embodiments, the dosage form comprises an additional agent.

In some embodiments, the additional agent is a pharmaceutically acceptable carrier. In some embodiments, the pharmaceutically acceptable carrier is selected from the group consisting of micelles, liposomes, microspheres, nanofibers, and any combination thereof.

In some embodiments, the additional agent is a pharmaceutically acceptable excipient. The compositions described herein comprise one or any combinations of excipients such as, but not limited to, diluents, binders, disintegrants, glidants, lubricants, colorants, flavouring agents, solvents, film forming polymers, plasticizers, opacifiers, antiadhesives, and polishing agents. In some embodiments, the pharmaceutically acceptable excipient is selected from the group consisting of a binder, filler, lubricant, dissolution aid, and any combination thereof. In some embodiments, the pharmaceutically acceptable excipient is selected from the group consisting of lactose, microcrystalline cellulose, silicon dioxide, titanium dioxide, stearic acid, starch, sodium starch glycolate, povidone, pregelatinized starch, croscarmellose, ethylcellulose, dicalcium phosphate, talc, sucrose, calcium stearate, hydroxypropylcellulose, hydroxypropyl methylcellulose, shellac, hydrogenated vegetable oil, beeswax, and any combination thereof.

In some embodiments, the compositions described herein are formulated using any of the following excipients or combinations thereof.

TABLE 1

Example excipients

| Excipient name | Chemical name | Exemplary Function |
|---|---|---|
| Avicel PH102 | Microcrystalline Cellulose | Filler, binder, wicking, disintegrant |
| Avicel PH101 | Microcrystalline Cellulose | Filler, binder, disintegrant |
| Eudragit RS-30D | Polymethacrylatel Poly(ethy acrylate, nethyl methacrylate, timethylammonioethyl methacrylate chloride) 1:2:0.1 | Film former, tablet binder, tablet diluent; Rate controlling polymer for extended release |

TABLE 1-continued

Example excipients

| Excipient name | Chemical name | Exemplary Function |
|---|---|---|
| Methocel K100M Premium CR | Hydroxypropyl methylcellulose | Rate controlling polymer for extended release; binder; viscosity-increasing agent |
| Methocel K100M | Hydroxypropyl methylcellulose | Rate controlling polymer for extended release; binder; viscosity-increasing agent |
| Talc | Talc | Dissolution control; anti-adherent, glidant |
| Triethyl Citrate | Triethyl Citrate | Plasticizer |
| Methocel E5 | Hydroxypropyl methylcellulose | Film-former |
| Opadry ® | Hydroxypropyl methylcellulose | One-step customized coating system which combines polymer, plasticizer and, if desired, pigment in a dry concentrate. |
| Surelease ® | Aqueous Ethylcellulose Dispersion | Film-forming polymer; plasticizer and stabilizers. Rate controlling polymer coating. |

In some embodiments, the magnesium compositions described herein include a carrier such as a solvent, dispersion media, coatings, antibacterial and antifungal agents, isotonic and absorption delaying agents. The use of such media and agents for pharmaceutically active substances is well known in the art. Acceptable salts can also be used in the composition, for example, mineral salts such as hydrochlorides, hydrobromides, phosphates, or sulfates, as well as the salts of organic acids such as acetates, proprionates, malonates, or benzoates. In some embodiments, the composition also contains liquids, such as water, saline, glycerol, and ethanol, as well as substances such as wetting agents, emulsifying agents, or pH buffering agents. Liposomes, such as those described in U.S. Pat. No. 5,422,120, PCT applications WO 95/13796, or WO 91/14445, or European patent EP 524,968 B1, may also be used as a carrier.

In some embodiments, a further material is added to the magnesium threonate as a compressibility augmenting agent. Such additional materials include silicon dioxides, non-silicon metal oxides, starches, starch derivatives, surfactants, polyalkylene oxides, cellulose A ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, pregelatinized starch, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional additives known to those skilled in the art can be added to the novel excipient prior to preparation of the final product. For example, if desired, any generally accepted soluble or insoluble inert filler (diluent) material can be included in the final product (e.g., a solid dosage form). In some embodiments, such inert fillers comprise a monosaccharide, a disaccharide, a polyhydric alcohol, inorganic phosphates, sulfates or carbonates, and/or mixtures thereof. Examples of suitable inert fillers include sucrose, dextrose, lactose, xylitol, fructose, sorbitol, calcium phosphate, calcium sulfate, calcium carbonate, microcrystalline cellulose, mixtures thereof, and the like.

In some embodiments, the composition comprises an excipient that is a swellable material such as a hydrogel in amounts that can swell and expand. Examples of swellable materials include hydrophilic polymers that are lightly cross-linked, such cross-links being formed by covalent or ionic bond, which interact with water and aqueous biological fluids and swell or expand to some equilibrium state. Swellable materials such as hydrogels exhibit the ability to swell in water and retain a significant fraction of water within its structure, and when cross-linked they will not dissolve in the water. Swellable polymers can swell or expand to a very high degree, exhibiting a 2 to 50 fold volume increase. Specific examples of hydrophilic polymeric materials include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like. Other examples of swellable materials include hydrogels exhibiting a cross-linking of 0.05 to 60%, hydrophilic hydrogels known as Carbopol.™ acidic carboxy polymer, Cyanamer.™ polyacrylamides, cross-linked water-swellable indene-maleic anhydride polymers, Good-rite.™ polyacrylic acid, polyethyleneoxide, starch graft copolymers, Aqua-Keeps.™ acrylate polymer, diester cross-linked polyglucan, and the like. Methods for testing swellable materials with regards to polymer imbibition pressure and hydrogel-water interface interaction are described in U.S. Pat. No. 4,327,725 issued May 4, 1982, titled "Osmotic device with hydrogel driving member".

In some embodiments, the dosage forms described herein also contains effective amounts of coloring agents, (e.g., titanium dioxide, F. D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

In some embodiments, the additional agent is a nutritionally active agent. In some embodiments, the nutritionally active agent is selected from the group consisting of a calcium-containing material, an herbal, a spice, vitamin A, vitamin B, vitamin C, vitamin D, vitamin E, vitamin K, niacin, folic acid, biotin, a mineral, and any combination thereof. In some embodiments, the additional agent is a threonate precursor.

An example of a fast release tablet (Formula A) is shown in Example 1. The Formula A tablet comprises magnesium L-threonate (450 mg) as magnesium composition, carnauba wax as binder, magnesium stearate as lubricant, and a coating comprising talc as inert powders and hydrogenated vegetable oil. A weight ratio of the carnauba wax to the magnesium stearate is 12.

Figure 1B:
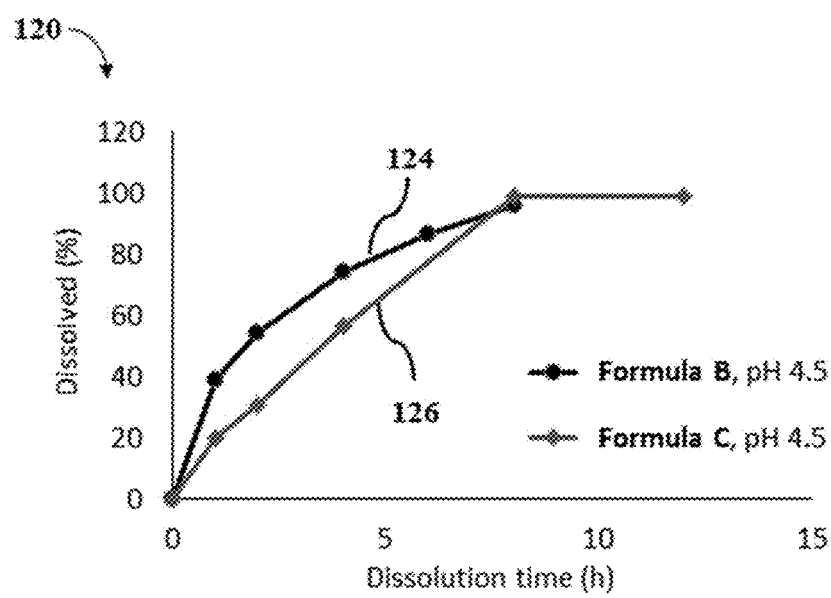
Figure 1C:
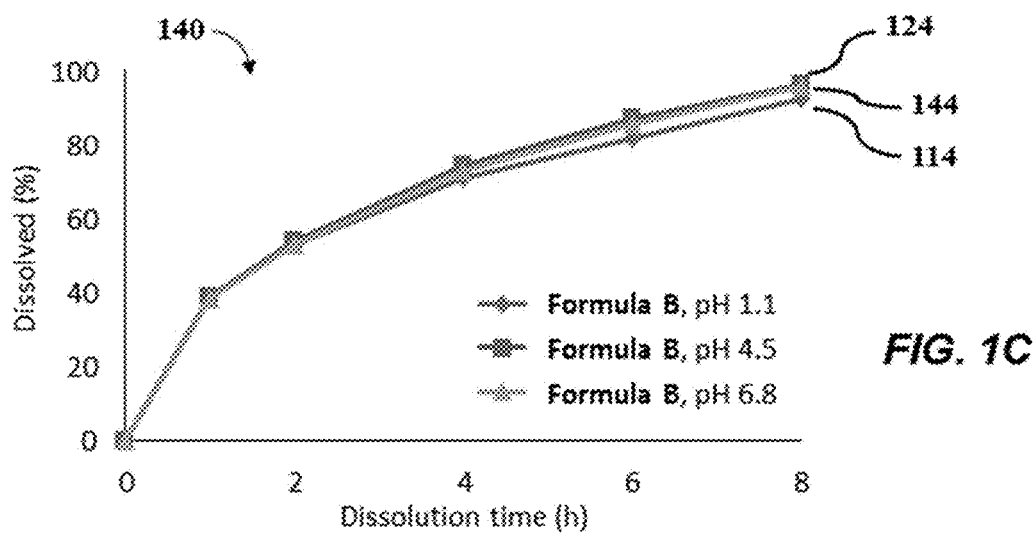

An example of a sustained release tablet (Formula B) is shown in Example 2. The Formula B tablet comprises magnesium L-threonate (500 mg) as magnesium composition, carnauba wax as binder, magnesium stearate as lubricant, and a coating comprising talc as inert powders and hydrogenated vegetable oil. A weight ratio of the carnauba wax to the magnesium stearate is 20. The in vitro dissolution profiles of Formula B in pH 1.1 (denoted as 114), 4.5 (denoted as 124) and 6.8 (denoted as 144) are shown in FIGS. 1A, 1B, and 1C. For Formula B, the release profile of threonic acid, which may be substantially equivalent to the release profile of magnesium, ranged between (i) about 10 to 50% in about 1 hour, (ii) about 10 to 60% in about 2 hours, (iii) about 20 to 80% in about 4 hours, (iv) about 50 to 90% in about 6 hours, and (v) greater than or equal to about 95% in about 8 hours as measured using a USP type II (paddle) dissolution system at 75 rpm, at a temperature of about 37° C., in pH 1.1, 4.5 and 6.8.

Figure 1D:
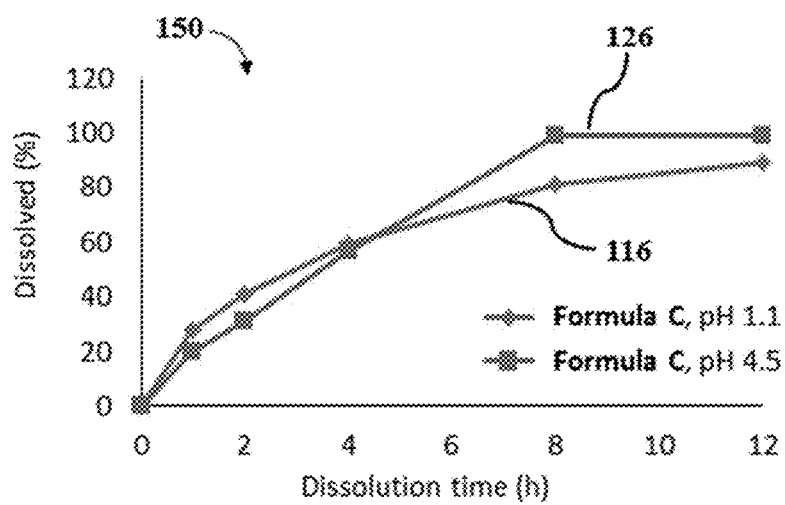

Another example of a controlled release tablet (Formula C) is shown in Example 3. The Formula C tablet comprises magnesium L-threonate (450 mg or 500 mg) as magnesium composition, povidone K-90 as binder, microcrystalline cellulose as glidant, colloidal silicon dioxide as filler, carbopol and carboxyl methyl cellulose as swellable materials, Starcap starch, magnesium stearate lubricant, and talc as inert powders. The in vitro dissolution profiles of Formula C in pH 1.1 (denoted as 116) and 4.5 (denoted as 126) are shown in FIGS. 1A, 1B, and 1D. For Formula C, the release profile of threonic acid, which may be substantially equivalent to the release profile of magnesium, ranged between (i) about 10 to 30% in about 1 hour, (ii) about 20 to 50% in about 2 hours, (iii) about 40 to 60% in about 4 hours, (iv) greater than or equal to about 70% in about 8 hours, and (v) greater than or equal to about 80% in about 12 hours as measured using a USP type II (paddle) dissolution system at 75 rpm, at a temperature of about 37° C., in pH 1.1 and 4.5.

Figure 6:
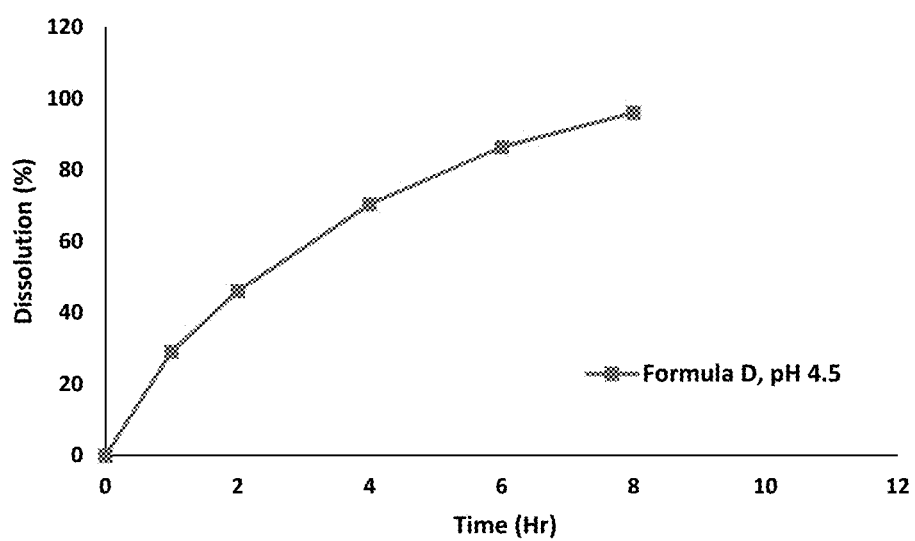
FIG. 6 shows a threonic acid dissolution profile of dosage forms comprising magnesium threonate.

Another example of a dosage form is shown in Example 7. The Formula D tablet comprises an intra-granular portion and an extra-granular portion. The in vitro dissolution profile of Formula D is shown in FIG. 6.

Figure 2A:
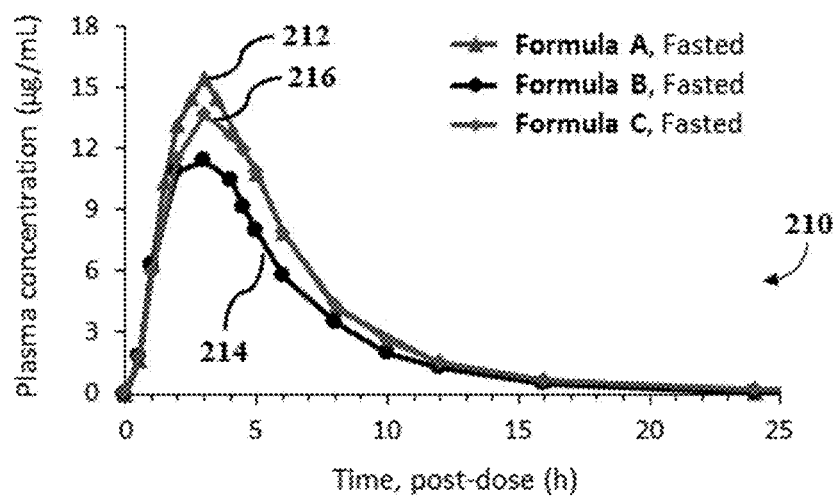
FIG. 2A-2F show plasma concentration profiles of dosage forms comprising magnesium threonate.
Figure 2B:
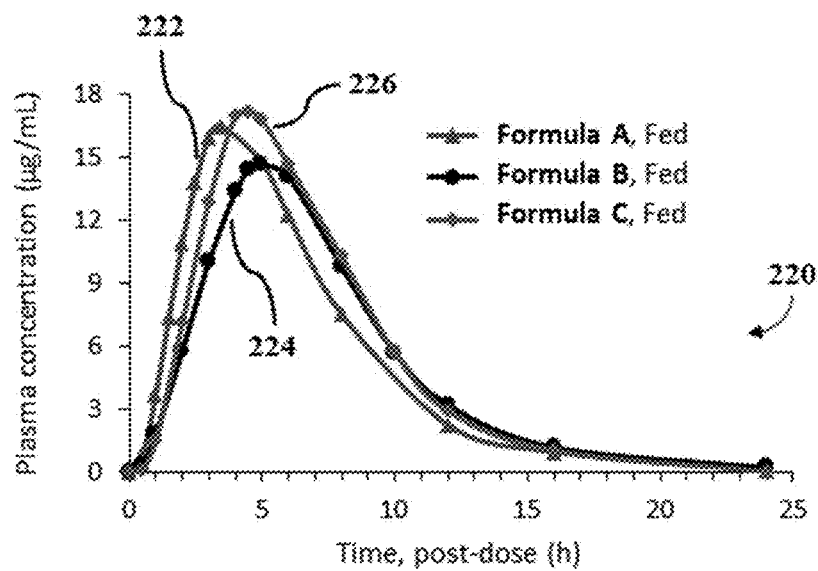
Figure 2C:
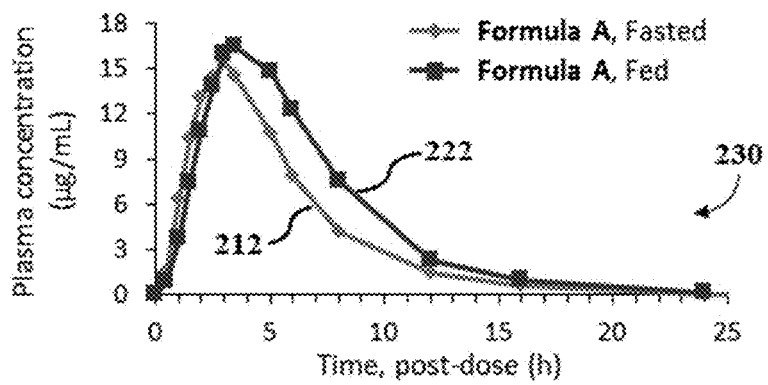
Figure 2D:
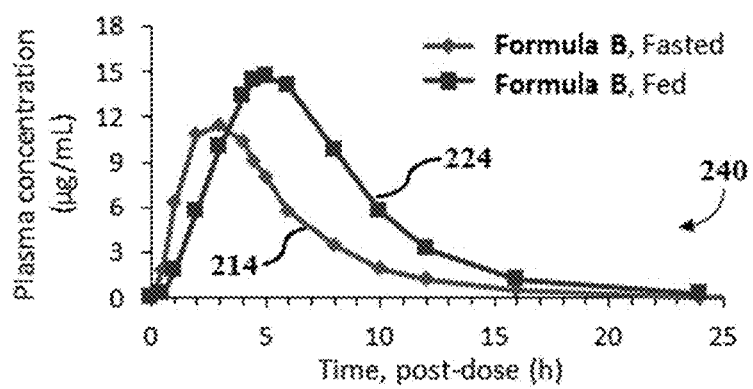
Figure 2E:
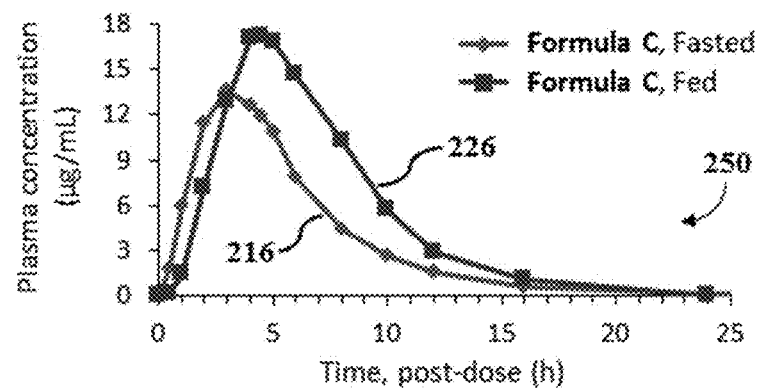
Figure 2F:
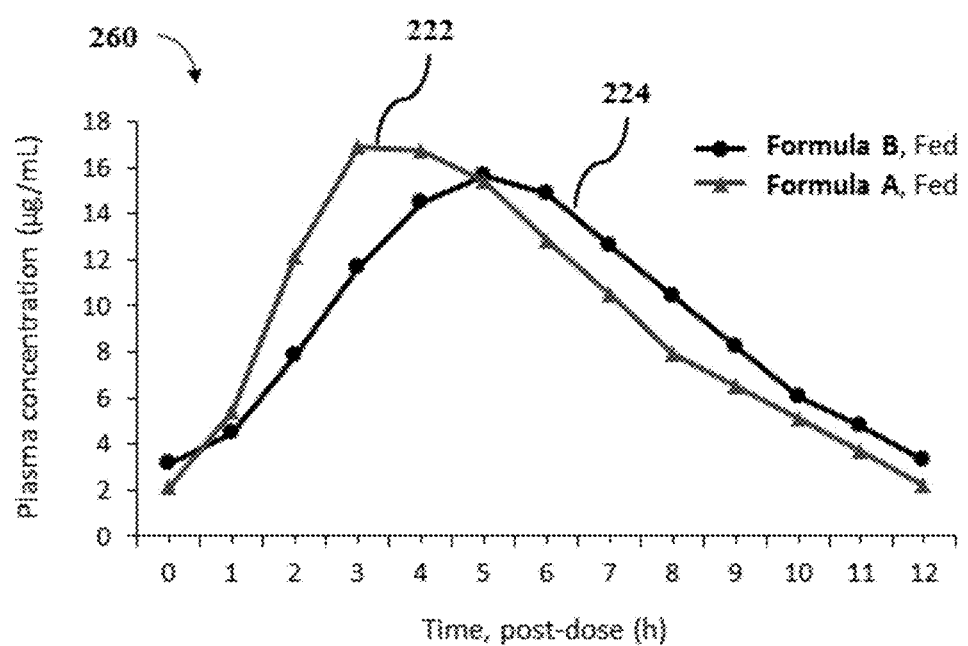

Examples of in vivo plasma concentration profiles of dosage forms comprising magnesium threonate (Formula A, Formula B, and Formula C) are shown in Example 4. In an experiment, human subjects received three tablets of either Formula A, Formula B, and Formula C, receiving a total of about 1350 to 1500 mg of magnesium L-threonate. Some of the subjects were fasted (fasted state) for at least 10 hours prior to the oral administration of the tablets. Some of the subjects consumed a high-fat, high calorie breakfast within 30 minutes ("fed state") before the oral administration of the tablets. Blood samples were collected at pre-dosing (baseline) and at a number of time intervals until 24 hours post-dosing. The resulting in vivo plasma concentration profiles are shown in FIG. 2A-2F. In a fasted state, the oral administration of Formula C exhibited the greatest mean $AUC_{0-24}$ (82.3 µg·h/mL) relative to that of Formula B (66.8 µg·h/mL) and Formula A (79.2 µg·h/mL) (FIG. 2A). In a fed state, the oral administration of Formula C exhibited the greatest mean $AUC_{0-24}$ (112.1 µg·h/mL) relative to that of Formula B (103.3 µg·h/mL) and Formula A (98.2 µg·h/mL) (FIG. 2B). For all three dosage forms (Formula A, Formula B, and Formula C), administration of the dosage forms when subjects were in a fed state yielded a higher mean $AUC_{0-24}$ than when subjects were in a fasted state (FIG. 2C-2E). In the fed state, the administration of Formula B yielded the lowest mean $C_{max}$ (16.1 µg·h/mL), and the highest mean $T_{max}$ (5.3 h) relative to that of Formula A or Formula C (Table 2). In the fed state, the in vivo plasma concentration profile of Formula B yielded a lower skewness value than that of Formula A (FIG. 2F). Not wishing to be bound by theory, a lower skewness of the in vivo plasma concentration profile of Formula B may indicate a slower release of the active ingredient (magnesium L-threonate) into circulation relative to that of Formula A.

Also provided is a method of treating a disease, disorder, syndrome, or condition in a patient in need thereof, comprising orally administrating a dosage form described herein.

In some embodiments, the dosage form comprising magnesium threonate is administered twice per day. In some embodiments, the dosage form is administered more than twice per day. The dosage form is administered three times or more per day. In some embodiments, the dosage form is administered at an interval of 12 hours.

In some embodiments, a daily administration of the dosage form is repeated for at least about 5 days (d). In some embodiments, the dosage form is administered for at least about 15 days. The daily administration of the dosage form is repeated for at least about 5 d, 6 d, 7 d, 8 d, 9 d, 10 d, 11 d, 12 d, 13 d, 14 d, 15 d, 16 d, 17 d, 18 d, 19 d, 20 d, 21 d, 22 d, 23 d, 24 d, 25 d or longer. In some embodiments, the administration of the dosage form is repeated once a week, twice a week, three times a week, four times a week, five times a week, six times a week, or seven times a week. In some embodiments, the administration of the dosage form is repeated once a month, twice a month, three times a month, four times a month, five times a month, six times a month, seven times a month, or more. In some embodiments, the administration of the dosage form (e.g., daily) is repeated for at least about 1 month, at least about 2 months, at least about 3 months, at least about 4 months, at least about 5 months, or at least about 6 months or longer. In some embodiments, the administration of the dosage form is repeated in a continuous manner over a lifetime.

In some embodiments, the dosage form is administered twice a day with food. In some embodiments, the dosage form is administered to a patient in a fed state. In some embodiments, the method further comprises subjecting the patient to a fast for at least about 4 hours after orally administrating the dosage form. In some embodiments, the dosage form is administered at an interval of 12 hours with food. In some embodiments, the patient consumes a meal about 0.5 h to about 4 h prior to the dosage form administration. In some embodiments, the patient consumes a meal at least about 0.5 h prior to the dosage form administration. In some embodiments, the patient consumes a meal at most about 4 h prior to the dosage form administration. In some embodiments, the patient consumes a meal about 0.5 h to about 1 h, about 0.5 h to about 1.5 h, about 0.5 h to about 2 h, about 0.5 h to about 2.5 h, about 0.5 h to about 3 h, about 0.5 h to about 3.5 h, about 0.5 h to about 4 h, about 1 h to about 1.5 h, about 1 h to about 2 h, about 1 h to about 2.5 h, about 1 h to about 3 h, about 1 h to about 3.5 h, about 1 h to about 4 h, about 1.5 h to about 2 h, about 1.5 h to about 2.5 h, about 1.5 h to about 3 h, about 1.5 h to about 3.5 h, about 1.5 h to about 4 h, about 2 h to about 2.5 h, about 2 h to about 3 h, about 2 h to about 3.5 h, about 2 h to about 4 h, about 2.5 h to about 3 h, about 2.5 h to about 3.5 h, about 2.5 h to about 4 h, about 3 h to about 3.5 h, about 3 h to about 4 h, or about 3.5 h to about 4 h prior to the dosage form administration. In some embodiments, the patient consumes a meal about 0.5 h, about 1 h, about 1.5 h, about 2 h, about 2.5 h, about 3 h, about 3.5 h, or about 4 h prior to the dosage form administration.

In some embodiments, the patient suffers from a disease, disorder, syndrome, or condition chosen from cardiovascular disease, neurodegenerative disorder, sleep disorder, neurological disorder, never damage, developmental disorder/autism spectrum disorder, autoimmune disease, genetic disorder, rheumatic disease, inflammatory disease, and physical trauma.

In some embodiments, the patient suffers from mild cognitive impairment, short-term memory loss, long-term memory loss, Alzheimer's disease, Parkinson's disease, Huntington's disease, autism, schizophrenia, cognitive decline, depression, dementia, attention deficit hyperactivity disorder (ADHD), amyotrophic lateral sclerosis (ALS), Multiple Sclerosis (MS), diabetes, cardiovascular disease, hypertension, migraine, glaucoma, mood disorder, stress, anxiety, depression, sleep disorder, psychosis, metabolic disorder, fatigue, cancer, HIV, hepatitis, spinal cord injury, post-surgery recovery, post-traumatic stress disorder, arthritis, neuropathic pain, inflammation, tremor, and fibromyalgia. In some embodiments, the patient suffers from cognitive decline as secondary effect of disease or medical treatment (HIV disease, cancer, chemotherapy). Magnesium supplementation may also be useful in maintaining, enhancing, and/or improving conditions which may result in loss of body magnesium, including, but not limited to, alcoholism, anorexia, bulimia, metabolic syndromes, and poor nutrition.

In some embodiments, the patient is an adult.

In some embodiments, the method further comprises determining a physiological concentration of threonic acid in the patient prior to orally administrating the dosage form comprising magnesium threonate. In some embodiments, the method further comprises determining at least one additional physiological concentration of threonic acid in the patient subsequent to orally administrating the dosage form. In some embodiments, the physiological concentration is serum concentration, plasma concentration, urine concentration, or cerebrospinal fluid concentration. In some embodiments, the at least one additional physiological concentration of threonic acid and/or magnesium is determined at about 0.5 h, about 1 h, about 1.5 h, about 2 h, about 2.5 h, about 3 h, about 3.5 h, about 4 h, about 4.5 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, and/or about 23 h post-dosing.

Dosage form B disclosed herein exhibits superior physiological effect as compared to a fast release dose (dosage form A) of magnesium threonate when administered in vivo. Such improved physiological effects including but not limited to mood improvement and cognitive function such as working memory, processing speed, and cognitive flexibility (see FIG. 5).

Figure 4:
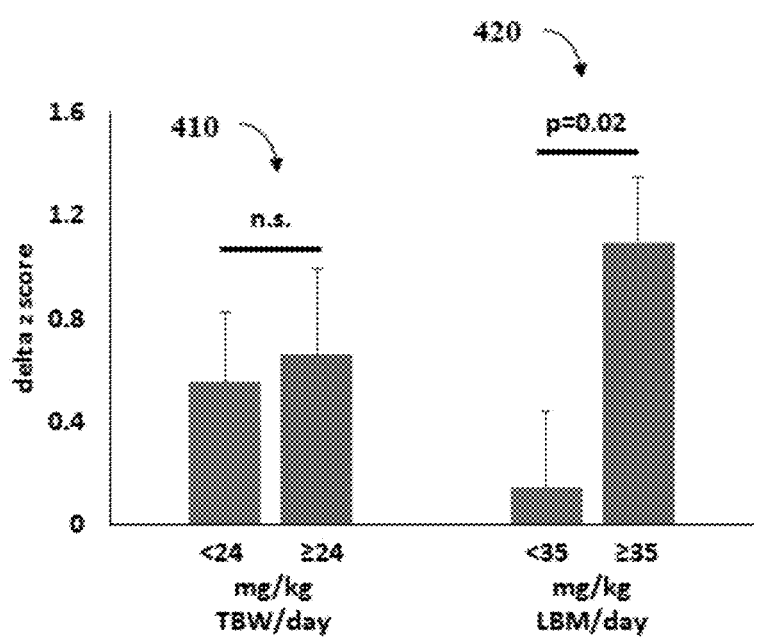
FIG. 4 illustrates neuropsychological test battery z-scores of patients treated with magnesium threonate administration based on total body weight (TBW) dosage or lean body mass (LBM) dosage.

An example of the effect of drug dosing by TBW and LBM of a subject is shown in FIG. 4. In two experiments, male and female human subjects received a dosage form comprising magnesium L-threonate daily for 9-12 weeks. In the first experiment, dosage of the dosage form was set to correspond to (1) approximately 1.5 g magnesium L-threonate per day (1.5 g/day) for subjects between 50 and 70 kg TBW, and (2) approximately 2 g magnesium L-threonate per day (2 g/day) for subjects between 70 and 100 kg TBW. Male and female subjects between the ages of 50-70 were administered magnesium L-threonate for 12 weeks. Following magnesium L-threonate administration, efficacy in improving overall cognitive ability was determined by change in performance on a Neuropsychological Test Battery (NTB) comprised of four validated cognitive tests, including executive function, working memory, attention, and episodic memory. The NTB score may be represented as a composite score of the combined standardized scores (z score) of the clinical trial population from the individual cognitive tests. In the second experiment, male and female patients with schizophrenia between the ages of 18-55 received 2 g magnesium L-threonate per day (2 g/day). Following magnesium L-threonate administration for 9 weeks, efficacy in improving overall cognitive ability was determined by change in performance on the MATRICS consensus cognitive battery (MCCB). MCCB can also be represented as a z score. To evaluate overall effects of magnesium L-threonate in the two studies, the data from the two studies were combined using z scores change from baseline. Subjects were categorized into high and low dosage groups which were defined based on the median dosage/ day by TBW and by LBM for all subjects in both studies. The median dosage/day by TBW was approximately 24 mg/kg TBW/day and the median dosage/day by LBM as approximately 35 mg/Kg LBM/day. When the subjects scores were categorized by high dosage and low dosage by TBW, subjects who received a high dosage of the drug (more than 24 mg/kg TBW/day) did not perform better than subjects who received a low dosage of the drug (less than 24 mg/kg TBW/day) (FIG. 4, plot 410). Alternatively, when the subjects were categorized by high dosage and low dosage by LBM, subjects who received a high dosage of the drug (more than 35 mg/kg LBM/day) exhibited a significantly higher improvement in the overall cognitive ability than subjects who received a low dosage of the drug (less than 35 mg/kg LBM/day) (FIG. 4B, plot 420). Not wishing to be bound by theory, an estimate dosage of magnesium threonate at about 35 mg/kg LBM/day for one or more days may be a minimum therapeutic dosage to improve cognitive ability.

Figure 5A:
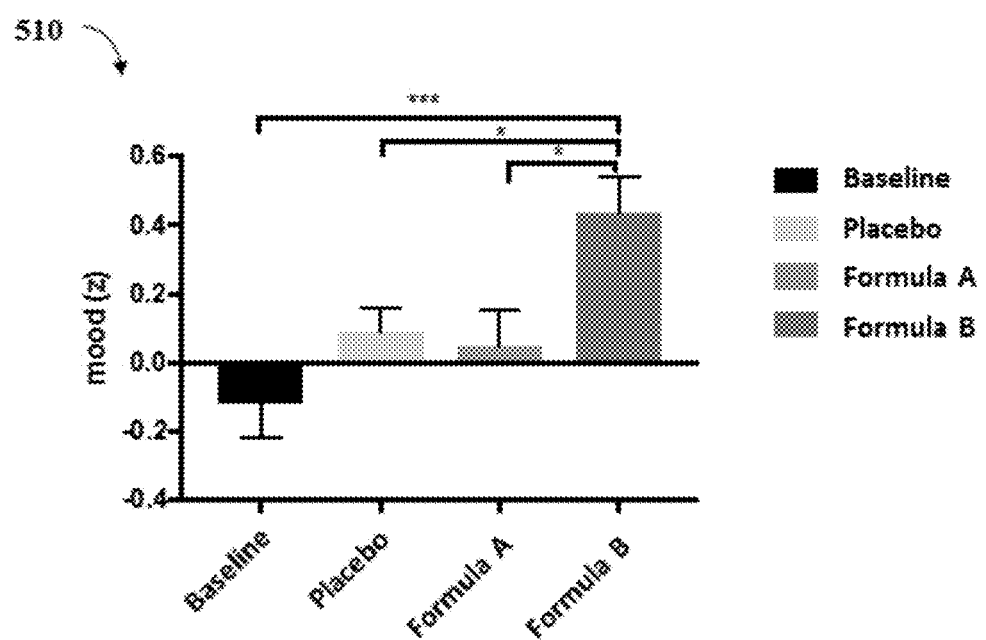
FIG. 5A-5C illustrates mood (anxiety and depression z-score), global cognition (z-score composite consisting of working memory, processing speed, and cognitive flexibility), and working memory (backwards digit span) respectively, of human subjects orally administered dosage forms comprising magnesium threonate.
Figure 5B:
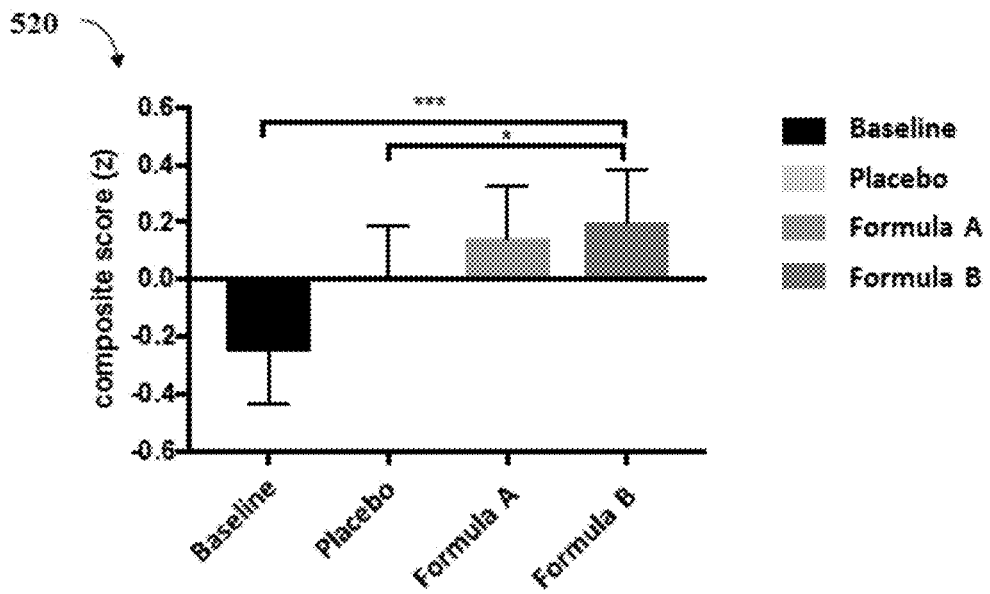
Figure 5C:
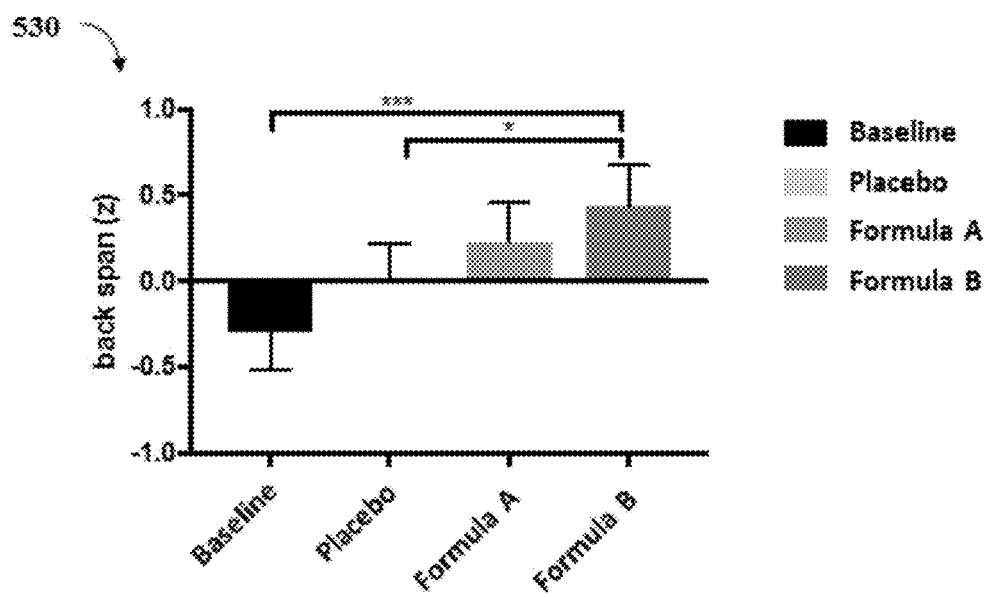

An example of differences in efficacy among different dosage forms is shown in FIG. 5. As indicated in FIG. 5A, subjects who were treated with the sustained release dosage form (Formula B), which has lower fluctuation index, exhibited a significantly better mood z-score than those who were treated with either the fast release dosage form (Formula A) or placebo (higher mood score indicates better mood). Additionally, as shown in FIGS. 5B and 5C, only the subjects who were treated with the sustained release dosage form (Formula B) exhibited a significantly higher composite z-score and back span z-score than those who were treated with placebo. Not wishing to be bound by theory, a dosage form with certain fluctuation index may effectively improve cognitive ability.

Also provided is a method of making a dosage form comprising magnesium threonate. In some embodiments, the method of making the dosage form comprises forming a mixture comprising the magnesium threonate and an additional agent. In some embodiments, the method of making the dosage form further comprises formulating the mixture to form the dosage form. In some embodiments, the dosage form comprises magnesium threonate in an amount between about 400 to 2000 mg.

Tablets are made by methods known in the art and, in some embodiments, further comprise suitable binders, fillers, lubricants, diluents, disintegrating agents (dissolution aids), colorants, flavoring agents, flow-inducing agents, melting agents, many varieties of which are known in the art. In some embodiments, the dosage forms have a film coating to protect the components of the magnesium-counter ion supplement composition from one or more of moisture, oxygen and light or to mask any undesirable taste or appearance. Suitable coating agents include, for example, cellulose, hydroxypropylmethyl cellulose, croscarmellose, and ethylcellulose. In some embodiments, the dosage form comprises a plurality of beads encapsulated in a capsule. Such format can be used as an extended release formulation. Other forms of tablets can also be formulated in extended release format. Methods of making extended release tablets, including controlled release and sustained release, are known in the art, e.g., see U.S. Patent Publications 2006/ 051416 and 2007/0065512, or other references disclosed herein.

In some embodiments, dosage form are made by mixing a powder comprising magnesium (Mg) and threonate (T), both of which can be present in a salt form, with a polymer in an amount sufficient to create particles comprising the magnesium (Mg), the threonate (T), and the polymer, wherein the particles are of a size sufficient to be retained by a 12 mesh sieve. In some embodiments, the method further comprising: filtering the particles to remove unbound threonate using the 12 mesh sieve; drying the particles; adding an acceptable amount of lubricant to the particles; compressing the particles into one or more pills of total size between about 100 mg and about 2000 mg and coating the one or more pills with a polymer coating comprising one or more of polyvinylpyrrolidone, polyvinyl acetate, and propylene glycol. In some embodiments, the pills are made with an elemental magnesium content of from about 10 mg to about 200 mg.

In some embodiments, the dosage forms comprise a plurality of beads, wherein each bead includes a core having a diameter from about 1 micrometer (km) to about 1000 m and the core includes an active ingredient comprising magnesium or a salt thereof in the range of about 15 to about 350 milligram (mg) of magnesium (Mg)/gram (g) of the dosage form, wherein the dosage forms include less than about 2.5% adduct and has a dissolution rate of the active ingredient of more than about 80% within about the first 60 minutes following entry of the dosage forms into a use environment. In some embodiments, the dissolution rate is more than about 80% within 30 minutes.

In some embodiments, each bead includes a core and an active ingredient comprising magnesium. In some embodiments, a suitable bead form of magnesium comprises magnesium and threonate admixed with soluble components, e.g., sugars (e.g., sucrose, mannitol, etc.), polymers (e.g., polyethylene glycol, hydroxypropyl cellulose, hydroxypropyl methyl cellulose, etc.), surfactants (sodium lauryl sulphate, chremophor, tweens, spans, pluronics, and the like), insoluble glidant components (microcrystalline cellulose, calcium phosphate, talc, fumed silica, and the like), coating material (examples of suitable coating materials are polyethylene glycol, hydroxypropyl methyl cellulose, wax, fatty acids, etc.), dispersions in suitable material (examples are wax, polymers, physiologically acceptable oils, soluble agents, etc.) or combinations of the above.

According to some embodiments, the core includes sugar spheres (nonpareil seeds), microcrystalline cellulose, or mannitol. In some embodiments, the core is a sugar sphere, USP (Paulaur Cranbury, N.J.). In some embodiments, the particle size of the core ranges from about 1 m to about 1000 μm. In some embodiments, the particle size of the core ranges from about 300 m to about 900 μm. In some embodiments, the particle size of the core ranges from about 450 m to about 825 μm. In some embodiments, the core is coated to avoid interaction between the core and the active ingredient. For example, suitable coating materials include, but are not limited to, polyethylene glycol, hydroxypropyl methyl cellulose, wax, fatty acids, etc.

In some embodiments, the spheres comprise a portion of the dosage form ranging from about 50 mg/g to about 500 mg/g, such as from about 60 mg elemental magnesium per g of dosage form (i.e., 60 mg Mg/g), to about 100 mg elemental magnesium per g of dosage form (i.e., 100 mg Mg/g). The fraction of the bead will depend on the amount of additional constituents, if any, used in the dosage form.

The core can be coated with magnesium, e.g., magnesium threonate. In some embodiments, magnesium threonate is present in amounts from about 150 mg/g (or 12.4 mg Mg/g) to about 950 mg/g (or 78.4 mg Mg/g), such as from about 500 to 900 mg/g (or 41.2 to 74.3 mg Mg/g) based on the weight of the entire fast release bead. In other embodiments, magnesium is present in amounts from about 15 to 300 mg/g, such as from about 25 to about 250 mg/g.

In some embodiments, magnesium threonate is added to a mixture of a binder and a glidant prior to coating the core. In some embodiments, the glidant is selected from, but is not limited to, microcrystalline cellulose, calcium phosphate, talc, and fumed silica. Glidants may be used in amounts ranging from 1.5 mg/g to about 35 mg/g. In some embodiments, glidants range from about 1.5 mg/g to about 30 mg/g. In some embodiments, glidants range from about 2.5 mg/g to about 25 mg/g. In some embodiments, the range of glidant is from about 5 mg/g to about 30 mg/g.

In some embodiments, the binder is selected from, but is not limited to, povidone (PVP), croscarmellose, ethylcellulose, hydroxypropyl methylcellulose (HPMC, Opadry), hydroxypropyl cellulose (HPC), or combinations thereof. In some embodiments where the binder is HPMC, the binder is present in an amount ranging from about 15 mg/g to about 30 mg/g, such as from about 15 mg/g to about 25 mg/g. In some embodiments, where the binder is povidone, the binder is present in an amount of from about 1.5 mg/g to about 35 mg/g, such as from about 5 mg/g to about 30 mg/g.

The mixture of active ingredient and binder/water/glidant may be prepared by mixing, e.g., with a stirrer, for at least 15 minutes, for at least 30 minutes, or for at least one hour. The components may also be combined by methods including blending, mixing, dissolution and evaporation, or by using suspensions.

In some embodiments, the active ingredient/binder/inactives mixture is deposited on a core, wet massed and extruded, granulated, or spray dried. In some embodiments, sugar spheres are prewarmed to a temperature ranging from about 40° C. to about 55° C. prior to application of the mixture. In some embodiments, the core is coated with from about 2% weight/weight (w/w) to about 10% w/w seal coating prior to applying the active layer. In some embodiments, the seal coating is any applicable coating which can separate any active ingredients from the core, for example, polymer coatings such as Eudragit®, HPMC, HPC, or combinations thereof.

In some embodiments, the sugar sphere are coated with a fluidized bed coater known in the art, for example, a Glatt Powder Coater and Granulator, GPCG3 (Ramsey, N.Y.). One skilled in coating conditions such as air velocity, spray rate, and atomization pressure are typically controlled as is appreciated by and known to those skilled in the art. In some embodiments, the temperature ranges from about 43° C. to about 51° C. In some embodiments, the air velocity ranges from about 5 to about 9 meter per second (m/s). The spray rate ranges from about 9 to about 42 gram per minute (g/min). The atomization pressure can range from about 1.5 to about 2.0 bar. The beads are then dried in the fluidized bed of the coating apparatus at a temperature of about 45° C. to about 50° C. for at least 5 minutes. In some embodiments, the beads are dried for at least 15 minutes, or for at least 30 minutes. One skilled in the art will recognize that many alternate operating conditions and various types of equipment can also be used.

Once the beads are formed as cores containing magnesium threonate as provided herein, the beads may be optionally additionally coated with a seal coating. In some embodiments, the seal coating is a polymer or a combination of polymers that can be designed to be pH dependent or independent. In some embodiments, the polymer for the seal coating is selected from, but are not limited to HPMC (Opadry®, Colorcon, Pa.), HPC, Eudragit® RL, Eudragit® E100, Eudragit® E 12.5, Eudragit®, E PO, Eudragit® NE (e.g., NE 30D or NE 40D) and combinations of two or more of the foregoing. These polymers are insoluble in aqueous media but display pH-independent swelling on contact with aqueous fluids. In some embodiments, the beads are coated with pH-dependent polymers, soluble at a pH such as above 5. In the fast release bead formulations, the seal coating polymer is present in amounts ranging from about 0% w/w to about 40% w/w, such sa from about 0% w/w to about 10% w/w, for example, from about 0% w/w to about 3% w/w.

Alternatively the cores are coated with a rapidly disintegrating or dissolving coat for aesthetic, handling, or stability purposes. Suitable materials are polyvinylpyrrolidone, hydroxypropyl cellulose, hydroxypropyl methyl cellulose, polyethylene glycol, polymethacrylates containing free amino groups, each may be with or without plasticizers, and with or without an antitack agent or filler. An addition of about 3% of the weight of the core as coating material is generally regarded as providing a continuous coat for this size range. In some embodiments, the over coating is a polymer selected from, but are not limited to HPMC (Opadry®, Colorcon, Pa.), HPC, Eudragit® RL, Eudragit® E100, Eudragit® E 12.5, Eudragit® E PO, Eudragit® NE and mixtures thereof.

In some embodiments, the beads or bead mixtures are used, for example, in suspensions, filled into capsules, compressed into tablets, or filled into sachets. One or more types of extended release beads can be mixed together and encapsulated, or used as a sprinkle on the subject's food. In some embodiments, the oral solid dosage form is any of these forms. In some embodiments, the dosage form is a capsule. In some embodiments, the beads are formulated into capsules with the use of an encapsulation machine. Various capsule sizes may be required to accommodate the strength and fill weight of the target formulations. Capsule size range from 00 to 5 for fill weights ranging from about 15 mg to about 630 mg.

The particle sizes of the fast release and extended release bead components in the dosage form depend on the technology used to prepare them. The particle sizes component range from submicron to 500 m for powder technologies (mixtures, spray drying, dispersions etc), 5 to 1700 m for coating technologies (Wurster®, top spray, bottom spray, spray drying, extrusion, layering, etc.), to 1-40 millimeter (mm) for tabletting technologies.

In addition to the active ingredients comprising magnesium and threonate, the dosage forms can comprise any numbers of physiologically acceptable excipients, depending in part on the extended release mechanism to be used. "Physiologically Acceptable" includes molecular entities and compositions that do not produce an adverse, allergic or other untoward reaction when administered to an animal, or a human, as appropriate, e.g., those that are pharmaceutically acceptable. "Physiologically Acceptable Carrier" includes micelles, liposomes, microspheres, nanofibers, and any combination thereof. The physiologically acceptable carrier includes any and all solvents, dispersion media, coatings, antibacterial and antifungal agents, isotonic and absorption delaying agents and the like. The use of such media and agents for physiologically active substances is well known in the art. Except insofar as any conventional media or agent is incompatible with the active ingredient, its use in the magnesium threonate compositions is contemplated. Supplementary active ingredients can also be incorporated into the compositions. "Physiologically Acceptable Salts" include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations.

By way of example, extended release oral formulation can be prepared using additional methods known in the art. For example, in some embodiments, a suitable extended release form of the magnesium threonate compositions provided herein is a matrix tablet or capsule composition. Suitable matrix forming materials include, for example, waxes (e.g., carnauba wax, bees wax, paraffin wax, ceresine, shellac wax, fatty acids, and fatty alcohols), oils (e.g., hydrogenated vegetable oil), hardened oils or fats (e.g., hardened rapeseed oil, castor oil, beef tallow, palm oil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. In some embodiments, tablets contain granulates, coated powders, or pellets. In some embodiments, tablets are multi-layered. Multi-layered tablets are useful when the active ingredients, e.g., different forms of magnesium and threonate, have markedly different pharmacokinetic profiles. Optionally, the finished tablet are coated or uncoated.

The coating composition typically contains an insoluble matrix polymer (approximately 15-85% by weight of the coating composition) and a water soluble material (e.g., approximately 15-85% by weight of the coating composition). Optionally an enteric polymer (approximately 1 to 99% by weight of the coating composition) is used or included. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (e.g., lactose, sucrose, fructose, mannitol and the like), salts (e.g., sodium chloride, potassium chloride and the like), organic acids (e.g., fumaric acid, succinic acid, lactic acid, and tartaric acid), and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, and polymethacrylates containing carboxyl groups.

In some embodiments, the coating composition is plasticised according to the properties of the coating blend such as the glass transition temperature of the main component or mixture of components or the solvent used for applying the coating compositions. Suitable plasticisers may be added from 0 to 50% by weight of the coating composition and include, for example, diethyl phthalate, citrate esters, polyethylene glycol, glycerol, acetylated glycerides, acetylated citrate esters, dibutylsebacate, and castor oil. If desired, the coating composition may include a filler. The amount of the filler may be 1% to approximately 99% by weight based on the total weight of the coating composition and may be an insoluble material such as silicon dioxide, titanium dioxide, talc, kaolin, alumina, starch, powdered cellulose, magnesium containing compound, or polacrilin potassium.

The coating composition may be applied as a solution or latex in organic solvents or aqueous solvents or mixtures thereof. If solutions are applied, the solvent may be present in amounts from approximate by 25-99% by weight based on the total weight of dissolved solids. Suitable solvents are water, lower alcohol, lower chlorinated hydrocarbons, ketones, or mixtures thereof. If latexes are applied, the solvent is present in amounts from approximately 25-97% by weight based on the quantity of polymeric material in the latex. The solvent may be predominantly water.

In some embodiments utilizing a spray-drying process, an aqueous dispersion of magnesium threonate and a compressibility augmenting agent (for example, a surfactant or silicon dioxide) is brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles may be approximately spherical in shape and may be relatively uniform in size, thereby possessing excellent flowability. The coprocessed particles are not necessarily uniform or homogeneous. Other drying techniques such as flash drying, ring drying, micron drying, tray drying, vacuum drying, radio-frequency drying, and possibly microwave drying, may also be used.

Alternatively, all or part of the excipient may be subjected to a wet granulation with an active ingredient. A representative wet granulation includes loading the novel excipient particles into a suitable granulator, such as those available from Baker-Perkins, and granulating the particles together with the active ingredient, such as using an aqueous granulating liquid. In some embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with other excipients commonly used by those skilled in the art, depending of course upon the requirements of the particular formulation.

The complete mixture, in an amount sufficient to make a uniform batch of tablets, may then subjected to tableting in a conventional production scale tableting machine at normal compression pressures for that machine, e.g., about 1500-10,000 pounds per square inch (lbs/sq in). The mixture should not be compressed to such a degree that there is subsequent difficulty in its hydration when exposed to gastric fluid.

In some embodiments, the compositions described herein are prepared using formulations as described in U.S. Pat.

Nos. 4,606,909, 4,769,027, 4,897,268, 5,395,626, 6,919,373, 6,923,800, 6,929,803, 6,939,556, 6,797,283, 6,764,697, and 6,635,268.

In addition to oral dosage forms, the compositions can be administered to a subject by any available and effective delivery systems. Such delivery systems include, but are not limited to, parenteral, transdermal, intranasal, sublingual, transmucosal, intra-arterial, or intradermal modes of administration in dosage unit formulations containing conventional nontoxic physiologically acceptable carriers, adjuvants, and vehicles as desired, such as a depot or a controlled release formulation. Depending on the route of administration, the composition may be formulated as a suppository, lotion, patch, or device (e.g., a subdermally implantable delivery device or an inhalation pump). The compositions may be optimized for particular types of delivery.

In some embodiments, magnesium threonate is delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable excipients as set out above. Compositions in acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, orally or nasally, from devices that deliver the formulation in an appropriate manner.

In some embodiments, the compositions may be administered transdermally as described generally in, e.g., U.S. Pat. Nos. 5,186,938 and 6,183,770, 4,861,800, 6,743,211, 6,945,952, 4,284,444, and WO 89/09051.

In some embodiments, the composition may be delivered via intranasal, buccal, or sublingual routes to the brain rather than by inhalation to enable transfer of the active agents through the olfactory passages into the CNS and reducing the systemic administration. Devices commonly used for this route of administration are included in U.S. Pat. No. 6,715,485.

Preparation of a compositions for delivery in a subdermally implantable device can be performed using methods known in the art, such as those described in, e.g., U.S. Pat. Nos. 3,992,518; 5,660,848; 5,756,115; 5,422,123; 5,601,845, 5,912,013, and 6,194,000.

EXAMPLES

Example 1

Preparation and Dissolution Profiles of Fast Release Tablets

An example of a fast release tablet (Formula A) is discussed. The Formula A tablet comprises magnesium L-threonate (450 mg) as magnesium composition, carnauba wax as binder, magnesium stearate as lubricant, and an aqueous moisture barrier coating. A weight ratio of the carnauba wax to the magnesium stearate is 12.

| Ingredients | Mg/tablet | %, wt/wt |
|---|---|---|
| Magnesium Threonate | 450 | 77.58 |
| Carnauba Wax | 120 | 20.69 |
| Magnesium Stearate, NF | 10 | 1.72 |
| Total | 580.00 | 100.00 |

Figure 7:
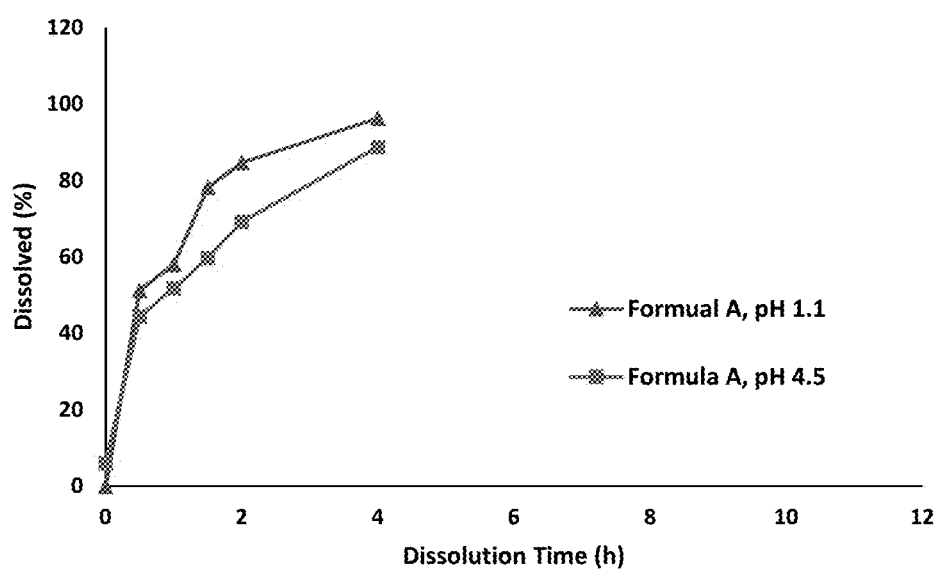
FIG. 7 shows a threonic acid dissolution profiles of dosage forms comprising magnesium threonate.

The release profile of Formula A tablets prepared above was examined in a USP type II (paddle) dissolution system at 75 rpm, at a temperature of about 37° C. in 0.1 N HCl (pH 1.1) or acetate buffer (pH 4.5). The amount of released threonic acid over time was measured using HPLC. The release profiles in pH 1.1 and 4.5 are shown in FIG. 7.

Example 2

Preparation and Dissolution Profiles of Sustained Release Tablets

An example of an extended release tablet (Formula B) is discussed. The Formula B tablet, a sustained release tablet, comprises magnesium L-threonate as magnesium composition, carnauba wax as binder, magnesium stearate as lubricant, and a coating comprising talc as inert powders and hydrogenated vegetable oil. A weight ratio of the carnauba wax to the magnesium stearate is 20. A formulation having 450 mg magnesium L-threonate was also prepared with the other excipients being the same.

| Ingredients | Mg/tablet | %, wt/wt |
|---|---|---|
| Magnesium Threonate | 500 | 70.42 |
| Carnauba Wax | 200 | 28.17 |
| Magnesium Stearate, NF | 10 | 1.41 |
| Total | 710 | 100.00 |

The release profile of Formula B tablets prepared above was examined in a USP type II (paddle) dissolution system at 75 rpm, at a temperature of about 37° C. in 0.1 N HCl (pH 1.1), acetate buffer (pH 4.5) or phosphate buffer (pH 6.8). The amount of released threonic acid over time was measured using HPLC. The release profiles in pH 1.1 (denoted as 114), 4.5 (denoted as 124) and 6.8 (denoted as 144) are shown in FIGS. 1A, 1B, and 1C.

Example 3

Preparation and Dissolution Profiles of Controlled Release Tablets

Another example of an extended release tablet formulation (Formula C) is discussed. The Formula C tablet, a controlled release tablet, comprises magnesium L-threonate, povidone K-90 as binder, microcrystalline cellulose as glidant, colloidal silicon dioxide as filler, carbopol and carboxyl methyl cellulose as swellable materials, Starcap starch, magnesium stearate lubricant, and talc as inert powders.

| Ingredients | Mg/tablet | %, wt/wt |
|---|---|---|
| Magnesium Threonate | 500.00 | 67.57 |
| Povidone K-90, USP (Plasdone ® K-90) | 44.4 | 6.00 |

-continued

| Ingredients | Mg/tablet | %, wt/wt |
|---|---|---|
| Microcrystalline Cellulose, NF (Avicel PH102) | 77.85 | 10.52 |
| Colloidal Silicon Dioxide, NF (CAB-O-SIL ® M-5P) | 6.22 | 0.84 |
| Carbopol 974 P | 40.7 | 5.50 |
| Carboxy methyl cellulose 7 HF, USP | 33.30 | 4.50 |
| Starcap 1500, NF | 25.09 | 3.39 |
| Talc Powder, USP | 6.22 | 0.84 |
| Magnesium Stearate, NF | 6.22 | 0.84 |
| Total | 740.00 | 100.00 |

The release profile of Formula C tablets prepared above was examined in a USP type II (paddle) dissolution system at 75 rpm, at a temperature of about 37° C. in 0.1 N HCl (pH 1.1) or acetate buffer (pH 4.5). The amount of released threonic acid over time was measured using HPLC. The amount of released magnesium over time was measured using ICP-MS. The release profiles in pH 1.1 (denoted as 116) and 4.5 (denoted as 126) are shown in FIGS. 1A, 1B, and 1D.

Example 4

Pharmacokinetic Study of Magnesium Threonate Dosages

The present example compares the fluctuation index of three dosage forms comprising magnesium threonate (Formula A, Formula B, and Formula C). Compared to the fast release dosage form (Formula A), the extended release dosage forms (Formula B and Formula C) aimed to promote a slower release of the active agent (magnesium and/or threonic acid). The extended release dosage forms intended to provide exposure of the active agent that would be sufficient for dosing once or twice a day.

Subjects and Methods

The concentration of L-threonic acid in the plasma of subjects dosed with a single dosage form (three tablets) of Formula A, Formula B, or Formula C was determined by HPLC. In a randomized crossover-manner, each of 12 male subjects received 1350 mg or 1500 mg of Formula A, Formula B, and Formula C (separated by a 3 day washout period). Plasma was collected from subjects receiving the single dosage form in a fasted state or in a fed state following a full meal. Fourteen plasma samples were collected over a 24 hour period for each subject at dosage form administration.

The plasma concentrations were used to generate PK curves and calculate the total amount of magnesium L-threonate exposure over 24 hours ($AUC_{0-24}$), the peak plasma concentration of L-threonic acid ($C_{max}$), the time to reach the peak plasma concentration of L-threonic acid ($T_{max}$) and the terminal half-life ($T_{1/2}$). The values presented in Table 2 are the averages of all subjects who completed dosing with all three formulas. $AUC_{0-24}$ and $C_{max}$ values were normalized to an effective dosage of 1500 mg. Any $AUC_{0-24}$ or $C_{max}$ value from a subject who received 1350 mg of the dosage form (three tablets that each comprises 450 mg magnesium L-threonate) was multiplied by a value of 10 divided by 9. Both $C_{max}$ and $T_{max}$ are the observed values and not calculated. In other words, among all the blood draw timepoints, for each subject the highest analyzed concentration was consider the $C_{max}$ and the corresponding timepoint was considered the $T_{max}$. $AUC_{0-24}$ was calculated for each subject using a rectangle approach with a left endpoint approximation using all timepoints for which a plasma concentration was obtained from 0 to 24 hours. The following equations were used for calculating $T_{1/2}$:

$$t_{\frac{1}{2}} = \frac{\ln 2}{k_e}$$

$$k_e = \frac{\ln C_{max} - \ln C_{last\ measurble\ concentraiton}}{(t_{last\ measurable\ concentration} - t_{max})}$$

where $k_e$ is elimination rate constant;
C is plasma concentration in µg/mL; and
t is time in hours (h).

To calculate the fluctuation value and the skewness of each curve, a theoretical steady state graph was generated to simulate repeat dosing, every 12 hours. To calculate the fluctuation index, concentration data from the first 12 hours after dosing (dosing interval) were used. The estimated fluctuation of the plasma concentration of L-threonic acid was calculated by subtracting the steady state minimum concentration from the steady state maximum concentration. Steady state was theoretically achieved by approximately 24 hours.

Skewness, which is the characterization of the degree of asymmetry of a distribution around its mean was calculated using the Excel SKEW function. Positive skewness indicates a distribution with an asymmetric tail extending toward more positive values and negative skewness indicates a distribution with an asymmetric tail extending toward more negative values. In order to use Excel SKEW function, the x-axis needs to be evenly distributed. Therefore, y values were estimated for x values at 1 hour intervals for 12 hours (hours 12-36 from the steady state curves).

TABLE 2

| | Formula A | | Formula B | | Formula C | |
|---|---|---|---|---|---|---|
| | Fasted | Fed | Fasted | Fed | Fasted | Fed |
| $C_{max}$ (µg/mL) | 16.4 ± 1.2 | 18.3 ± 1.4 | 12.3 ± 0.7 | 16.1 ± 1.3 | 14.9 ± 1.3 | 20.4 ± 1.5 |
| $C_{min}$ (µg/mL) | 1.4 ± 0.1 | 2.3 ± 0.2 | 1.3 ± 0.1 | 3.2 ± 0.4 | 1.6 ± 0.2 | 2.9 ± 0.4 |
| $T_{max}$ (h) | 2.8 ± 0.2 | 4.0 ± 0.4 | 2.9 ± 0.2 | 5.3 ± 0.2 | 3.2 ± 0.3 | 4.7 ± 0.5 |
| $T_{1/2}$ (h) | 3.0 ± 0.1 | 2.9 ± 0.2 | 3.0 ± 0.2 | 3.3 ± 0.2 | 3.3 ± 0.2 | 2.7 ± 0.1 |
| AUC over 24 hours (µg · h/mL) | 79.2 ± 6.7 | 98.2 ± 6.0 | 66.8 ± 4.8 | 103.3 ± 6.9 | 82.3 ± 7.9 | 112.1 ± 6.9 |
| AUC % change with food | 24.0 | | 54.6 | | 36.2 | |

TABLE 2-continued

|  | Formula A | | Formula B | | Formula C | |
| --- | --- | --- | --- | --- | --- | --- |
|  | Fasted | Fed | Fasted | Fed | Fasted | Fed |
| Fluctuation Index (%) | 214.1 ± 7.5 | 177.8 ± 9.8 | 201.0 ± 7.0 | 151.5 ± 9.7 | 200.1 ± 9.8 | 185.9 ± 13.3 |
| Steady State Skewness |  | 0.222 |  | 0.128 |  |  |
| Cavg | 7.1 ± 0.6 | 8.8 ± 0.5 | 5.6 ± 0.3 | 8.3 ± 0.4 | 6.8 ± 0.6 | 9.2 ± 0.4 |

Table 3 shows the concentrations scaled to what it would be for a therapeutic dose for a patient. The table above shows the data from the pharmacokinetic study (24 mg/kg LBM/dosage). Table 3 shows values scaled to a 17.5 mg/kg LBM/dosage.

TABLE 3

|  | Formula A | | Formula B | | Formula C | |
| --- | --- | --- | --- | --- | --- | --- |
|  | Fasted | Fed | Fasted | Fed | Fasted | Fed |
| $C_{max}$ (μg/mL) | 12.0 ± 0.9 | 13.3 ± 1.0 | 9.0 ± 0.5 | 11.7 ± 1.0 | 10.9 ± 1.0 | 14.9 ± 1.1 |
| $C_{min}$ (μg/mL) | 1.0 ± 0.1 | 1.7 ± 0.1 | 0.9 ± 0.1 | 2.3 ± 0.3 | 1.2 ± 0.1 | 2.1 ± 0.3 |
| AUC over 24 hours (μg · h/mL) | 57.8 ± 4.9 | 71.6 ± 4.4 | 48.7 ± 3.5 | 75.3 ± 5.0 | 60.0 ± 5.7 | 81.7 ± 5.0 |
| Cavg | 5.2 ± 0.4 | 6.4 ± 0.4 | 4.1 ± 0.2 | 6.1 ± 0.3 | 5.0 ± 0.4 | 6.7 ± 0.3 |

Example 5

Dosage Estimation

The present example compares the dosage of magnesium L-threonate that is provided in a dosage form. The effect of magnesium L-threonate treatment on human cognitive ability was assessed by a threshold based on the total body weight (TBW) of each subject and the lean body mass (LBM) of each subject.

In two experiments, male and female human subjects received a dosage form comprising magnesium L-threonate daily for 9-12 weeks. In the first experiment, dosage of the dosage form was set to correspond to (1) approximately 1.5 g magnesium L-threonate per day (1.5 g/day) for subjects between 50 and 70 kg TBW, and (2) approximately 2 g magnesium L-threonate per day (2 g/day) for subjects between 70 and 100 kg TBW. Male and female subjects between the ages of 50-70 were administered magnesium L-threonate for 12 weeks. Following magnesium L-threonate administration, efficacy in improving overall cognitive ability was determined by change in performance on a Neuropsychological Test Battery (NTB) comprised of four validated cognitive tests, including executive function, working memory, attention, and episodic memory. The NTB score may be represented as a composite score of the combined standardized scores (z score) of the clinical trial population from the individual cognitive tests.

In the second experiment, male and female patients with schizophrenia between the ages of 18-55 received 2 g magnesium L-threonate per day (2 g/day). Following magnesium L-threonate administration for 9 weeks, efficacy in improving overall cognitive ability was determined by change in performance on the MATRICS consensus cognitive battery (MCCB). MCCB can also be represented as a z score.

To evaluate overall effects of magnesium L-threonate in the two studies, the data from the two studies were combined using z scores change from baseline. Subjects were categorized into high and low dosage groups which were defined based on the median dosage/day by TBW and by LBM for all subjects in both studies. The median dosage/day by TBW was approximately 24 mg/kg TBW/day and the median dosage/day by LBM as approximately 35 mg/Kg LBM/day. When the subjects scores were categorized by high dosage and low dosage by TBW, subjects who received a high dosage of the drug (more than 24 mg/kg TBW/day) did not perform better than subjects who received a low dosage of the drug (less than 24 mg/kg TBW/day) (FIG. 4, plot 410). Alternatively, when the subjects were categorized by high dosage and low dosage by LBM, subjects who received a high dosage of the drug (more than 35 mg/kg LBM/day) exhibited a significantly higher improvement in the overall cognitive ability than subjects who received a low dosage of the drug (less than 35 mg/kg LBM/day) (FIG. 4B, plot 420).

Two-sample T-tests compared efficacy in low dosage and high dosage groups based on TBW and LBM. As shown in Table 4, there was no difference in the efficacy in the low dosage and high dosage groups based on TBW (p=0.81). On the other hand, as shown in Table 5, when scaled by LBM, efficacy in the high dosage group was significantly higher than efficacy in the low dosage group (p=0.02). These data indicate that dosage should be scaled by LBM.

TABLE 4

|  | Less than 24 mg/kg TBW/day | More than 24 mg/kg TBW/day |
| --- | --- | --- |
| Mean | 0.555151267 | 0.658768487 |
| Variance | 2.024563476 | 2.190081227 |
| Observations | 28 | 20 |
| Pooled Variance | 2.092929503 |  |
| Hypothesized Mean Difference | 0 |  |
| df | 46 |  |
| t Stat | −0.244640316 |  |
| P (T <= t) one-tail | 0.403911477 |  |
| t Critical one-tail | 1.678660414 |  |
| P (T <= t) two-tail | 0.807822954 |  |
| t Critical two-tail | 2.012895599 |  |

TABLE 5

|  | Less than 35 mg/kg LBM/day | More than 35 mg/kg LBM/day |
|---|---|---|
| Mean | 0.143185114 | 1.093042495 |
| Variance | 2.205300506 | 1.484766019 |
| Observations | 25 | 23 |
| Pooled Variance | 1.860697056 | |
| Hypothesized Mean Difference | 0 | |
| df | 46 | |
| t Stat | −2.410093383 | |
| P (T <= t) one-tail | 0.010002298 | |
| t Critical one-tail | 1.678660414 | |
| P (T <= t) two-tail | 0.020004595 | |
| t Critical two-tail | 2.012895599 | |

Example 6

Improving Mood and Cognition

The present example compares the in vivo efficacy of two dosage forms comprising magnesium threonate (Formula A and Formula B), which two dosage forms exhibit different in vivo plasma concentration profiles. Formula B exhibits the lower fluctuation index compared to Formula A and C disclosed herein and lower skewness. The two dosage forms were compared in terms of improving mood and cognition in human subjects.

Subjects and Methods

A single center, double-blinded, randomized, four-way crossover study in 22 healthy male and female subjects, ages 35-72 (inclusive) was performed. Consented subjects completed online questionnaires to evaluate their sleep and mood and cognitive ability. Subjects with subjective sleep and mood complaints were included. Sleep complaints needed to include problems with sleep maintenance.

Dosage was based on subject lean body mass (LBM). Dosage was approximately 20 mg/kg LBM/day (half of full day 40 mg/kg LBM/day dosage) single dosage, specific for nighttime only dosing. The subjects received either magnesium L-threonate or placebo for 5 days, in a randomized order, each separated by a 2-day washout. Each study period including washout covered one week.
Period A: baseline (one week no administration)
Period B: single nighttime dose of magnesium L-threonate Formula A (1-3 of 450 mg tablets).
Period C: placebo matching Formula A
Period D: single nighttime dose of magnesium L-threonate Formula B (1-3 of 450 mg tablets)
Period E: placebo matching Formula B The study duration was 35 days (Day 1 through the last diary entry on day 35). Subjects completed daily sleep and mood diaries in the morning and evening and at the end of each dosing period (prior to washout), subjects completed a computerized Neuropsychological Test Battery (NTB). Cognitive tests included in the NTB were trail making test (TMT), digit span (backward), Digit Symbol Substitution Test (DSST).

Daily sleep diary included morning questions about sleep quality and refreshed feeling, and evening questions about mood (anxiety and depression), external factors affecting mood (emotionally charged events and workload). All diaries were completed online daily within one hour of going to sleep and waking up. Cognitive tests were completed online on day 6 of each study period.

Statistical Methods 15 subjects were included in the data analysis—those who completed the study and whose dosage was in compliance with the protocol throughout the study. Individual cognitive test scores were converted to standardized z scores. Z scores were calculated using the study population baseline values. To generate a subject's composite cognitive score, the subject's z-scores from three tests were averaged at each time point. Cognitive Composite scores at 5 periods (baseline and 4 administration periods) for all subjects were compared by multilevel linear model. A general linear model with treatment as fixed factor, and age, sex, mood as covariates were used (SPSS statistics subscription). Anxiety and depression questions in daily sleep diary were converted to z scores for each subject using all values for each subject. Anxiety and depression scores were calculated for each period by averaging day 3 through 5. Anxiety and depression z scores were averaged for each subject each study period to generate a mood z-score. The mood score for the different administrations (baseline, MgT formula A, formula B, placebo A, placebo B) were compared by multilevel linear model in which the treatment was a fixed factor and daily emotional charge, workload, and sleep quality were covariates. P less than 0.05 was considered significant. Results of this study are shown in FIG. 5A-5C.

Example 7

Preparation and Dissolution Profiles of Tablets

Another example of a tablet dosage form (Formula D) having a two-part intra granular component and an extra-granular component as set forth in Table 6 was prepared.

TABLE 6

| Materials | Composition (%) | mg/tablet (mg) | Batch formula (g) | Qty Dispensed (g) |
|---|---|---|---|---|
| Part 1 Intra-granular Ingredients | | | | |
| Magnesium L-threonate | 53.20% | 532.0 | 1000.0 | N/A |
| Silica Dioxide (Aerosil 200 Pharma) | 2.00% | 20.0 | 37.6 | N/A |
| Klucel EXF | 4.00% | 40.0 | 75.2 | N/A |
| METHOCEL K4M | 2.40% | 24.0 | 45.1 | N/A |
| Magnesium Stearate | 1.00% | 10.0 | 18.8 | N/A |
| Subtotal | 62.6% | 626.00 | 1176.7 | N/A |

TABLE 6-continued

| Materials | Composition (%) | mg/tablet (mg) | Batch formula (g) | Qty Dispensed (g) |
|---|---|---|---|---|
| Part 2 Intra-granular Ingredients | | | | |
| Carnauba Wax | 10.0% | 100.0 | 188.0 | N/A |
| Dicalcium phosphate, Anhydrous | 10.70% | 107.0 | 201.1 | N/A |
| Klucel EXF | 2.00% | 20.0 | 37.6 | N/A |
| METHOCEL K4M | 4.70% | 47.0 | 88.3 | N/A |
| Magnesium Stearate | 0.25% | 2.5 | 4.7 | N/A |
| Subtotal | 27.7% | 276.5 | 519.7 | N/A |
| Extra-granular Ingredients | | | | |
| Klucel EXF | 9.00% | 90.0 | 169.2 | N/A |
| Magnesium Stearate | 0.75% | 7.5 | 14.1 | N/A |
| Total | 100.0% | 1000.0 | 1879.7 | N/A |

The tablets are prepared by pre-blending each of parts 1 and 2 of the intragranular ingredients. Each part is then subjected to roller compaction and the parts are combined. The extra-granular portion is then added and the tablets are formed using a production scale tableting machine at normal compression pressures.

The release profile of Formula D tablets prepared above was examined in a USP type II (paddle) dissolution system at 75 rpm, at a temperature of about 37° C. in 0.1 N HCl (pH 1.1) or acetate buffer (pH 4.5). The amount of released threonic acid over time was measured using HPLC. The release profiles are shown in FIG. 6.

Another example of a tablet dosage form (Formula D) having a one-part intra-granular component and an extra-granular component as set forth in Table 7 was prepared.

TABLE 7

| Materials | Composition (%) | mg/tablet (mg) | Batch formula (g) | Qty Dispensed (g) |
|---|---|---|---|---|
| Intra-granular Ingredients | | | | |
| Magnesium L-Threonate | 53.20% | 532.0 | 212.8 | 212.8 |
| Silica Dioxide (Aerosil 200 Pharma) | 2.00% | 20.0 | 8.0 | 8.0477 |
| Klucel EXF | 5.00% | 50.0 | 20.0 | 20.0388 |
| METHOCEL K4M | 3.00% | 30.0 | 12.0 | 12.0467 |
| Magnesium Stearate | 1.00% | 10.0 | 4.0 | 4.0482 |
| Total | 64.2% | 642.00 | 256.8 | 256.9814 |
| Extra-granular Ingredients | | | | |
| Carnauba Wax | 10.0% | 100.0 | 40.0 | 37.6998 |
| Dicalcium phosphate, Anhydrous | 10.70% | 107.0 | 42.8 | 40.3327 |
| Klucel EXF | 11.10% | 111.0 | 44.5 | 41.9407 |
| METHOCEL K4M | 3.00% | 30.0 | 12.0 | 11.3160 |
| Magnesium Stearate | 1.00% | 10.0 | 4.0 | 3.7771 |
| Total | 100.0% | 1000.0 | 400.0 | 392.05 |
| OPADRY amb II 88A180040 WHITE | 4.00% | N/A | 60.0 | 60.00 |

Table 8 provides dissolution data of the formulations above.

TABLE 8

| Formulation | Time (hrs) | | | | |
|---|---|---|---|---|---|
| | 1.00 | 2.00 | 4.00 | 6.00 | 8.00 |
| One-part intra-granular/ extra-granular formulation of Table 7 | 31.66 | 50.04 | 75.57 | 90.62 | 98.24 |
| Two-part intra-granular/ extra-granular formulation of Table 6 | 28.22 | 45.25 | 68.84 | 84.64 | 94.09 |
| | 29.12 | 46.94 | 71.91 | 88.29 | 98.05 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A dosage form comprising magnesium threonate and a controlled release carrier, wherein:
    at least a portion of magnesium (Mg) and threonate (T) of said magnesium threonate is present in a salt form of $MgT_2$;
    said magnesium threonate is present in an amount between about 200 to 6000 mg; and
    said controlled release carrier is present in the dosage form in an amount sufficient to provide an in vivo plasma profile that exhibits a fluctuation index that is less than about 170%.

2. The dosage form of claim 1, wherein said dosage form provides an in vivo plasma profile comprising a mean AUC0-24 of at least about 50 μg×h/mL.

3. The dosage form of claim 1, wherein said dosage form provides an in vivo plasma profile comprising a mean AUC0-24 of at least about 50 μg×h/mL, 80 μg×h/mL, 90 μg×h/mL, 100 μg×h/mL, 110 μg×h/mL, 120 μg×h/mL, 130 μg×h/mL, 140 μg×h/mL, 150 μg×h/mL, 160 μg×h/mL, 170 μg×h/mL, 180 μg×h/mL, 190 μg×h/mL, 200 μg×h/mL, 300 μg×h/mL, 400 μg×h/mL, or 500 μg×h/mL.

4. The dosage form of claim 1, wherein said dosage form provides an in vivo plasma profile comprising a mean AUC0-24 of from about 100 μg×h/mL to about 500 μg×h/mL, about 100 μg×h/mL to about 200 μg×h/mL, or about 103 μg×h/mL to about 120 μg×h/mL.

5. The dosage form of claim 1, wherein said controlled release carrier is present in said dosage form in an amount sufficient to provide an in vivo plasma profile that exhibits a mean $T_{max}$ of at least about 4.5 hours.

6. The dosage form of claim 1, wherein said dosage form provides an in vivo plasma profile comprising a mean AUC0-24 of at least about 50 μg×h/mL and a mean Tmax of at least about 4.5 hours.

7. The dosage form of claim 1, wherein said controlled release carrier is present in the dosage form in an amount sufficient to provide an in vivo plasma profile that exhibits a skewness that is less than about 0.2.

8. The dosage form of claim 1, wherein said dosage form provides an in vivo plasma profile comprising a mean AUC0-24 of at least about 50 μg×h/mL and a skewness that is less than about 0.2.

9. The dosage form of claim 1, wherein said dosage form provides an in vivo plasma profile comprising a mean AUC0-24 of at least about 50 μg×h/mL and wherein said controlled release carrier is present in the dosage form in an amount sufficient to provide for a fluctuation value (Cmax−Cmin) of less than about 14 μg/mL, 13 μg/mL, 12 μg/mL, 11 μg/mL, 10 μg/mL, 9 μg/mL, 8 μg/mL, 7 μg/mL, 6 μg/mL, 5 μg/mL, or lower.

10. The dosage form of claim 1, wherein said dosage form provides an in vivo plasma profile comprising a mean AUC0-24 of at least about 50 μg×h/mL and wherein said controlled release carrier is present in the dosage form in an amount sufficient to provide for a fluctuation value (Cmax−Cmin) of from about 14 μg/mL to about 5 μg/mL, from about 12 μg/mL to about 8 μg/mL, from about 11 μg/mL to about 9 μg/mL, or from about 11 μg/mL to about 10 μg/mL.

11. The dosage form of claim 1, wherein said dosage form provides an in vivo plasma profile comprising a mean AUC0-24 of at least about 50 μg×h/mL and wherein said controlled release carrier is present in the dosage form in an amount sufficient to provide for a mean fluctuation value (Cmax−Cmin) of less than about 10 μg/mL.

12. The dosage form of claim 1, wherein said dosage form provides an in vivo plasma profile comprising a mean AUC0-24 of at least about 50 μg×h/mL and wherein said controlled release carrier is present in the dosage form in an amount sufficient to provide for a ratio of mean fluctuation value to $C_{min}$ of less than about 14 μg/mL to 3.2±0.4 μg/mL.

13. The dosage form of claim 1, wherein said dosage form provides an in vivo plasma profile comprising a mean AUC0-24 of at least about 50 μg×h/mL and wherein said controlled release carrier is present in the dosage form in an amount sufficient to provide for a ratio of mean fluctuation value to $C_{min}$ of less than about 14 μg/mL to 2.3±0.3 μg/mL.

14. The dosage form of claim 1, wherein said controlled release carrier is present in said dosage form in an amount sufficient to provide an in vivo plasma profile of threonic acid comprising a mean $C_{avg}$ of between about 5 μg/mL to about 20 μg/mL.

15. The dosage form of claim 1, wherein said controlled release carrier is present in said dosage form in an amount sufficient to provide an in vivo plasma profile of threonic acid comprising a mean $C_{avg}$ of 4.1±0.2, 5.6±0.3, 6.1±0.3, or 8.3±0.4.

16. The dosage form of claim 1, wherein said magnesium threonate is present in an amount effective for the treatment of a disease, disorder, syndrome and/or condition, in the individual in need thereof.

17. The dosage form of claim 1, wherein said magnesium threonate is present in an amount of from about 400 to 2000 mg.

18. The dosage form of claim 1, wherein the controlled release carrier comprises one or more excipients.

19. The dosage form of claim 18, wherein the one or more excipients comprises carnauba wax.

* * * * *